United States Patent
Damrau et al.

(10) Patent No.: US 7,193,099 B2
(45) Date of Patent: *Mar. 20, 2007

(54) RACEMOSELECTIVE PREPARATION OF ISOLABLE ANSA-METALLOCENE BIPHENOXIDE COMPLEXES

(75) Inventors: Hans-Robert-Hellmuth Damrau, Constance (DE); Patrik Müller, Frankfurt (DE); Valerie Garcia, Compiègne (FR); Christian Sidot, Compiègne (FR); Christian Tellier, Compiègne (FR); Jean-François Lelong, Tracy-le-Mont (FR)

(73) Assignee: Basell Polyolefine GmbH, Wesseling (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/532,570

(22) PCT Filed: Oct. 22, 2003

(86) PCT No.: PCT/EP03/11680

§ 371 (c)(1),
(2), (4) Date: Apr. 25, 2005

(87) PCT Pub. No.: WO2004/037539

PCT Pub. Date: May 6, 2004

(65) Prior Publication Data

US 2006/0052587 A1   Mar. 9, 2006

Related U.S. Application Data

(60) Provisional application No. 60/432,202, filed on Dec. 10, 2002.

(30) Foreign Application Priority Data

Oct. 25, 2002  (DE) .............................. 102 50 061

(51) Int. Cl.
*C07F 17/00* (2006.01)
*B01J 31/00* (2006.01)
*C08F 4/44* (2006.01)

(52) U.S. Cl. .............................. 556/11; 556/1; 556/12; 556/43; 556/53; 556/58; 526/126; 526/160; 502/103; 502/117

(58) Field of Classification Search .............. 556/1, 556/11, 12, 43, 53, 58; 526/126, 160; 502/103, 502/117
See application file for complete search history.

(56) References Cited

U.S. PATENT DOCUMENTS 4,380,676 A    4/1983  Rasberger 4,985,576 A    1/1991  Rohrmann et al.
6,262,286 B1   7/2001  Gregorius et al.
6,992,204 B2 * 1/2006  Damrau et al. ............... 556/53
2004/0010157 A1 1/2004 Damrau et al.

FOREIGN PATENT DOCUMENTS

| DE | 100 30 638 | 1/2002 |
| EP | 0 035 965 | 9/1981 |
| EP | 0 397 499 | 11/1990 |
| EP | 0 700 935 | 3/1996 |
| WO | WO-92/09545 | 6/1992 |
| WO | WO-9915538 | 4/1999 |
| WO | WO-02/00672 | 1/2002 |

OTHER PUBLICATIONS

Waymouth, R. et al., "Enantioselective Hydrogenation of Olefins with Homogeneous Ziegler-Natta Catalysts", J. Am. Chem. Soc. 112 (1990), pp. 4911-4914.
Schmidt, K. et al., "Photochemical Isomerization of $Me_2Si$-Bridged Zirconocene Complexes, Application to Stereoselective Syntheses of *ansa*—Zirconocene Binaphtholate Stereoisomers", Organometallics, vol. 16, No. 8 (1997), pp. 1724-1728.
Damrau, H-R.H. et al., "Racemo-Selective Synthesis of *ansa*-Zirconocene Derivatives from Zirconium Biphenolate Complexes", Organometallics, vol. 20, No. 25 (2001), pp. 5258-5265.
Coates, G. et al., "Enantioselective Cyclopolymerization: Optically Active Poly(methylene-1,3-cyclopentane)", J. Am. Chem. Soc. 113 (1991), pp. 6270-6271.
Rheingold, A. et al., "Preparation and Properties of Chiral Titanocene and Zirconocene Dichloride Complexes of a Chiral Ligand", Organometallics, vol. 11 (1992), pp. 1869-1876.
van der Linden et al., "Polymerization of α-Olefins and Butadiene and Catalytic Cyclotrimerization of 1-Alkynes by a New Class of Group IV Catalysts. Control of Molecular Weight and Polymer Microstructure via Ligant Tuning in Sterically Hindered Chelating Phenoxide Titanium and Zirconium Species", J. Am. Chem. Soc. 117 (1995), pp. 3008-3021.
Kaminsky W. et al., "Asymmetric oligomerization of propene and 1 butene with a zirconocene-aluminoxane catalyst" Angew. Chem. 101 1989 Nr.9, pp. 1304 to 1306. (See Abstract).

* cited by examiner

*Primary Examiner*—Porfirio Nazario-Gonzalez
(74) *Attorney, Agent, or Firm*—Jarrod N. Raphael

(57) ABSTRACT

The invention relates to a process for preparing racemic metallocene biphenoxide complexes by reacting bridged transition metal complexes with cyclopentadienyl derivatives of alkali metals or alkaline earth metals and heating the reaction mixture obtained in this way to a temperature in the range from −78 to 250° C., to the corresponding metallocene biphenoxide complexes and to their use as catalysts or as constituents of catalysts for the polymerization of olefinically unsaturated compounds or as reagents or catalysts in stereoselective synthesis.

19 Claims, No Drawings

RACEMOSELECTIVE PREPARATION OF ISOLABLE ANSA-METALLOCENE BIPHENOXIDE COMPLEXES

RELATED APPLICATIONS

This application is a national stage application (under 35 U.S.C. 371) of PCT/EP2003/011680 filed Oct. 22, 2003 which claims benefit to German application 102 50 061.4 filed Oct. 25, 2002 and U.S. provisional application 60/432,202 filed Dec. 10, 2002.

The present invention relates to a process for preparing racemic ansa-metallocene biphenoxide complexes having relatively short isomerization times by reacting bridged transition metal complexes of the formula (I)

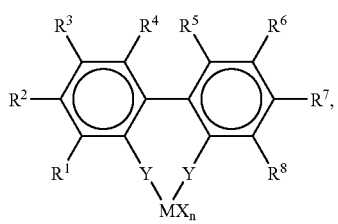

where the substituents and indices have the following meanings:

M is titanium, zirconium, hafnium, vanadium, niobium, tantalum, chromium, molybdenum, tungsten or an element of transition group III of the Periodic Table and the lanthanides, X are identical or different and are each fluorine, chlorine, bromine, iodine, hydrogen, $C_1$–$C_{10}$-alkyl, $C_6$–$C_{15}$-aryl, alkylaryl having from 1 to 10 carbon atoms in the alkyl part and from 6 to 20 carbon atoms in the aryl part, —$OR^9$ or —$NR^9{}_2$, where $R^9$ are identical or different and are each $C_1$–$C_{10}$-alkyl, $C_6$–$C_{15}$-aryl, $C_3$–$C_{10}$-cycloalkyl, alkylaryl, n is an integer from 1 to 4 and corresponds to the valence of M minus 2, $R^1$, $R^2$, $R^4$, $R^5$, $R^7$, $R^8$ are identical or different and are each hydrogen, fluorine, chlorine, bromine, iodine, $C_1$–$C_{20}$-alkyl, 3- to 8-membered cycloalkyl which may in turn bear a $C_1$–$C_{10}$alkyl group as substituent, $C_6$–$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part, —$OR^{10}$, —$SR^{10}$, —$N(R^{10})_2$, —$P(R^{10})_2$ or $Si(R^{10})_3$, where $R^{10}$, are identical or different and are each $C_1$–$C_{10}$-alkyl, $C_6$–$C_{15}$-aryl, $C_3$–$C_{10}$-cycloalkyl, alkylaryl, where the radicals mentioned may be partially or fully substituted by heteroatoms, $R^3$, $R^6$ are identical or different and are each hydrogen, —$OR^{11}$, —$SR^{11}$, —$N(R^{11})_2$, —$P(R^{11})_2$ or $Si(R^{11})_3$, where $R^{11}$ are identical or different and are each $C_1$–$C_{10}$-alkyl, $C_3$–$C_{10}$-cycloalkyl, Y are identical or different and are each

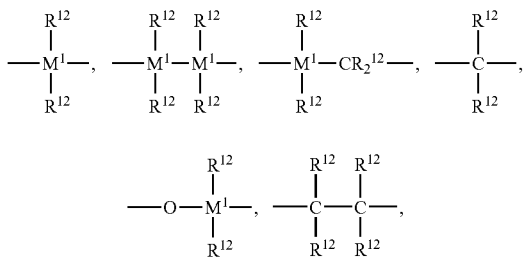

=$BR^{12}$, =$AlR^{12}$, —Ge—, —Sn—, —O—, —S—, =SO, =$SO_2$, =$NR^{12}$, =CO, =$PR^{12}$ or =$P(O)R^{12}$, where $R^{12}$ are identical or different and are each hydrogen, halogen, $C_1$–$C_{10}$alkyl, $C_1$–$C_{10}$fluoroalkyl, $C_6$–$C_{10}$-fluoroaryl, $C_6$–$C_{10}$-aryl, $C_1$–$C_{11}$-alkoxy, $C_2$–$C_{10}$-alkenyl, $C_7$–$C_{40}$-arylalkyl, $C_8$–$C_{40}$-arylalkenyl, $C_7$–$C_{40}$-alkylaryl, or two radicals $R^{12}$ together with the atoms connecting them form a ring, $M^1$ is silicon, germanium or tin, with cyclopentadienyl derivatives of alkali metals or alkaline earth metals and heating the reaction mixture obtained in this way to a temperature in the range from –78 to 250°C., with or without addition of free radicals or free radical formers to give racemic metallocene complexes of the formula (II)

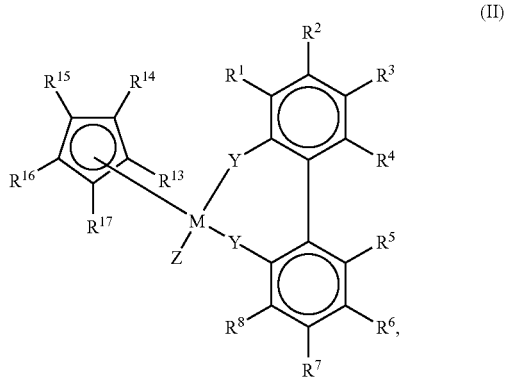

where Y, M and $R^1$ to $R^8$ are as defined above and $R^{13}$ to $R^{17}$ are identical or different and are each hydrogen, $C_1$–$C_{20}$-alkyl, 5- to 7-membered cycloalkyl which may in turn bear a $C_1$–$C_{10}$-alkyl group as substituent, $C_6$–$C_{15}$-aryl or arylalkyl, where adjacent radicals may together form cyclic groups having from 4 to 15 carbon atoms, or $Si(R^{18})_3$, where $R^{18}$ are identical or different and are each $C_1$–$C_{10}$-alkyl, $C_6$–$C_{15}$-aryl or $C_3$–$C_{10}$-cycloalkyl, and Z is

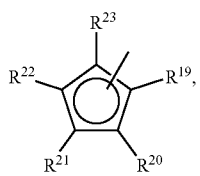

where the radicals
$R^{19}$ to $R^{23}$ are identical or different and are each hydrogen, $C_1$–$C_{20}$-alkyl, 5- to 7-membered cycloalkyl which may in turn bear a $C_1$–$C_{10}$-alkyl group as substituent, $C_6$–$C_{15}$-aryl or arylalkyl, where adjacent radicals may together form cyclic groups having from 4 to 15 carbon atoms, or $Si(R^{24})_3$ where
$R^{24}$ are identical or different and are each $C_1$–$C_{10}$-alkyl, $C_6$–$C_{15}$-aryl or $C_3$–$C_{10}$-cycloalkyl, or the radicals
$R^{16}$ and Z together form a -[T(R^{25})(R^{26})]$_m$-E- group, where
T may be identical or different and are each silicon, germanium, tin or carbon,
$R^{25}$, $R^{26}$ are each hydrogen, $C_1$–$C_{10}$-alkyl, $C_3$–$C_{10}$-cycloalkyl or $C_6$–$C_{15}$-aryl
m is 1, 2, 3 or 4, and
E is

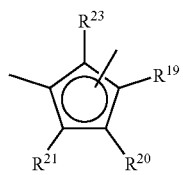

or A, where
A is

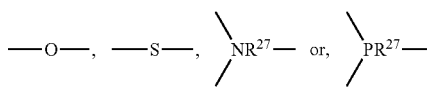

where $R^{27}$ are identical or different and are each $C_1$–$C_{10}$-alkyl, $C_6$–$C_{15}$-aryl, $C_3$–$C_{10}$-cycloalkyl, alkylaryl or $Si(R^{28})_3$
where $R^{28}$ are identical or different and are each $C_1$–$C_{10}$-alkyl, $C_6$–$C_{15}$-aryl, $C_3$–$C_{10}$-cycloalkyl or alkylaryl,
to corresponding racemic metallocene biphenoxide complexes of the formula (II) and to the use of racemic metallocene biphenoxide complexes of the formula (II) as catalysts or as constituents of catalyts for the polymerization of olefinically unsaturated compounds or as reagents or as catalysts in stereoselective synthesis.

Apart from stereospecific olefin polymerization, enantioselective organic synthesis is increasingly offering interesting possible applications for chiral metallocene complexes of metals of transition groups III–VI of the Periodic Table of the Elements. An example is the enantioselective hydrogenation of prochiral substrates, for example prochiral olefins as described in R. Waymouth, P. Pino, J. Am. Chem. Soc. 112 (1990), p. 4911–4914, or prochiral ketones, imines and oximes, as described in WO 92/9545.

Mention may also be made of the preparation of optically active alkenes by enantioselective oligomerization, as described in W. Kaminsky et al., Angew. Chem. 101 (1989), p. 1304–1306, and the enantioselective cyclopolymerization of 1,5-hexadienes, as described in R. Waymouth, G. Coates, J. Am. Chem. Soc. 113 (1991), p. 6270–6271.

The abovementioned applications generally require the use of a metallocene complex in its racemic form, i.e. without meso compounds. In the case of the diastereomer mixture (rac and meso form) obtained in the metallocene synthesis of the prior art, the meso form firstly has to be separated off. Since the meso form has to be discarded, the yield of racemic metallocene complex is low.

Attempts have therefore been made in the past to develop racemoselective syntheses of ansa-metallocenes. A significant step in racemoselective syntheses of ansa-metallocenes proceeds via the intermediate of an ansa-metallocene bisphenoxide or an ansa-metallocene biphenoxide. Corresponding synthetic routes of a general type are described, for example, in WO 99/15538 and in DE 10030638.

Despite the progress achieved, a generally applicable reaction scheme for the racemoselective synthesis of ansa-metallocenes has not been found hitherto. In the synthetic route via the intermediate of the ansa-metallocene bisphenoxides, the racemoselectivity of the synthetic route is highly dependent on the substitution pattern of the bisindenyl ligands used. Thus, the ansa-metallocene bisphenoxide intermediates can usually be obtained racemoselectively only when using derivatives substituted in the 2 position of the bridged bisindenyl ligand. Without being tied to a particular theory, it is assumed that the reaction path possibly proceeds via a kinetically controlled mechanism in which two different diastereomeric transition states having different energies are formed, so that the two isomers, namely the meso form and the racemate form, are formed in different amounts.

However, this synthetic route using 2,6-methyl-substituted phenoxides via the intermediate of the ansa-metallocene bisphenoxide has not been able to be applied successfully to more highly substituted and more sterically hindered ansa-bisindenyl ligand complexes. The use of phenoxide auxiliary ligands substituted in the 4 position of the phenoxide generally leads only to slight racemate excesses.

In all the synthetic routes via such ansa-metallocene bisphenoxide intermediates, the bisphenoxide complexes are thermally stable as soon as they are formed so that no isomerization between rac and meso form occurs when the phenoxide auxiliary ligands are replaced.

In contrast, the situation is different in the case of the ansa-metallocene biphenoxide complexes. The corresponding synthetic route using substituted biphenoxides as auxiliary ligands, in which a dilithium salt of an ansa-ligand is reacted with a dichlorozirconium biphenoxide complex, generally leads initially to a rac/meso ratio of the ansa-metallocene biphenoxide complexes formed of from about 1:1 to 5:1. However, in this case the meso diastereomer can be isomerized completely or virtually completely into the thermodynamically more stable rac isomer by heating. The differences in the thermodynamic stability of the two diastereomers is due to steric repulsions of the ligand system having the bulky substituents generally employed in the 3 and 3' positions of the biphenoxide ligand. It is assumed that the primary reaction path to the ansa-metallocene biphenoxide complex is likewise kinetically controlled.

This strategy for the racemoselective preparation of ansa-metallocene biphenoxide complexes can be applied in the case of various metals and also in the case of a wide variety of different ligands. However, this synthetic route has the disadvantage that the tert-butyl-substituted biphenoxide auxiliary ligands which have mainly been used in the past, for example 3,3',5,5'-tetra-tert-butylbiphenol, require relatively long reaction times at high temperatures for the thermal isomerization. In general, reaction times of up to 10 hours in toluene or similar solvents at temperatures of about 100° C. are used for the racemoselective synthesis of ansa-metallocene biphenoxide complexes. The long reaction times and the high temperatures for the isomerization both lead to sometimes considerable losses in yield, and to a corresponding, disadvantageous consumption of time and energy.

A further disadvantage of the known syntheses using the multiply alkyl-substituted biphenoxide auxiliary ligands customarily employed is the relatively high solubility of these nonpolar complexes in the aromatic solvents usually employed, which makes isolation of the complex in pure form by crystallization considerably more difficult.

It is an object of the present invention to overcome the disadvantages of the prior art and find a process for the selective preparation of racemic metallocene biphenoxide complexes which are virtually free of mesoisomer (NMR measurement accuracy). In particular, it is an object of the present invention to find a racemoselective process for synthesizing metallocene biphenoxide complexes which leads in a simple and cost-effective manner to end products which can be isolated in pure form. A further object is to find racemic metallocene complexes which either can be used directly as or in catalysts, primarily for olefin polymerization, or after modification, for example by replacement of an "auxiliary ligand", can be used as or in catalysts, primarily for olefin polymerization, or can be used as reagents or catalysts in stereoselective synthesis.

We have found that this object is achieved by the process defined in the claims, by the racemic metallocene complexes 11 and by their use as catalysts or in catalysts for the polymerization of olefinically unsaturated compounds or as reagents or catalysts in stereoselective synthesis.

The terms "meso form", "racemate" and thus also "enantiomers" in the context of metallocene complexes are known and are defined, for example, in Rheingold et al., Organometallics 11 (1992), p. 1869–1876.

For the purposes of the present invention, the term "virtually meso-free" means that more than 80%, preferably at least 90%, of a compound are present in the form of the racemate, particularly preferably at least 95%.

It has surprisingly been found that metallocene biphenoxide complexes having polar substituents and/or substituents capable of electron delocalization, preferably with one or more free electron pairs, in the 5 or 5' position of the biphenoxide ligand lead to significantly shorter isomerization times. Furthermore, these biphenoxide complexes can be isolated and crystallized significantly more easily.

The bridged transition metal complexes used in the process of the present invention have the formula (I)

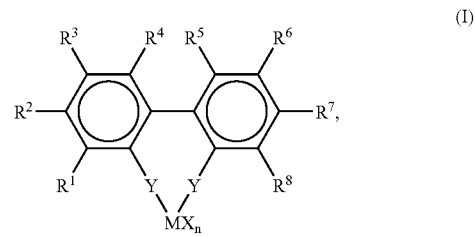

where the substituents and indices have the following meanings:

M is titanium, zirconium, hafnium, vanadium, niobium, tantalum, chromium, molybdenum, tungsten or an element of transition group III of the Periodic Table and the lanthanides, X are identical or different and are each fluorine, chlorine, bromine, iodine, hydrogen, $C_1$–$C_{10}$-alkyl, $C_6$–$C_{15}$-aryl, alkylaryl having from 1 to 10 carbon atoms in the alkyl part and from 6 to 20 carbon atoms in the aryl part, —$OR^9$ or —$NR^9_2$, where $R^9$ are identical or different and are each $C_1$–$C_{10}$-alkyl, $C_6$–$C_{15}$-aryl, $C_3$–$C_{10}$-cycloalkyl, alkylaryl, n is an integer from 1 to 4 and corresponds to the valence of M minus 2, $R^1$, $R^2$, $R^4$, $R^5$, $R^7$, $R^8$ are identical or different and are each hydrogen, fluorine, chlorine, bromine, iodine, $C_1$–$C_{20}$-alkyl, 3- to 8-membered cycloalkyl which may in turn bear a $C_1$–$C_{10}$-alkyl group as substituent, $C_6$–$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part, —$OR^{10}$, —$SR^{10}$, —$N(R^{10})_2$, —$P(R^{10})_2$ or $Si(R^{10})_3$, where $R^{10}$ are identical or different and are each $C_1$–$C_{10}$-alkyl, $C_6$–$C_{15}$-aryl, $C_3$–$C_{10}$-cycloalkyl, alkylaryl, where the radicals mentioned may be partially or fully substituted by heteroatoms, $R^3$, $R^6$ are identical or different and are each hydrogen, —$OR^{11}$, —$SR^{11}$, —$N(R^{11})_2$, —$P(R^{11})_2$ or $Si(R^{11})_3$, where $R^{11}$ are identical or different and are each $C_1$–$C_{10}$-alkyl, $C_3$–$C_{10}$-cycloalkyl, Y are identical or different and are each

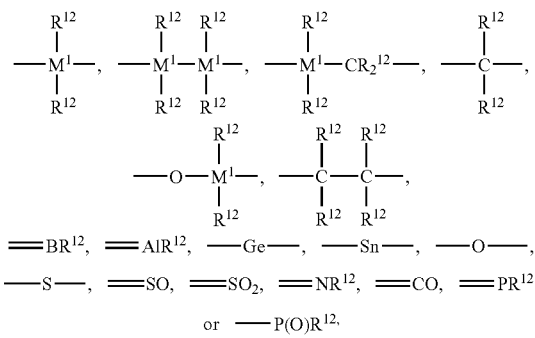

where $R^{12}$ are identical or different and are each hydrogen, halogen, $C_1$–$C_{10}$-alkyl, $C_1$–$C_{10}$-fluoroalkyl, $C_6$–$C_{10}$-fluoroaryl, $C_6$–$C_{10}$-aryl, $C_1$–$C_{10}$-alkoxy, $C_2$–$C_{10}$-alkenyl, $C_7$–$C_{40}$-arylalkyl, $C_8$–$C_{40}$-arylalkenyl, $C_7$–$C_{40}$-alkylaryl, or two radicals $R^{12}$ together with the atoms connecting them form a ring, $M^1$ is silicon, germanium or tin.

Preferred metals M are titanium, zirconium and hafnium, in particular zirconium.

Well-suited substituents X are fluorine, chlorine, bromine, iodine, preferably chlorine, also $C_1$–$C_6$-alkyl such as methyl, ethyl, n-propyl, isopropyl, n-butyl, sec-butyl, i-butyl, preferably tert-butyl. Further well-suited substituents X are alkoxides —$OR^9$ or amides —$N(R^9)_2$, where $R^9$ are identical or different and are each $C_1$–$C_{10}$-alkyl, $C_6$–$C_{15}$-aryl, alkylaryl, arylalkyl, fluoroalkyl or fluoroaryl each having from 1 to 10 carbon atoms in the alkyl radical and from 6 to 20 carbon atoms in the aryl radical. Such radicals X are, for example, methyl, ethyl, i-propyl, tert-butyl, phenyl, naphthyl, p-tolyl, benzyl, trifluoromethyl, pentafluorophenyl.

The substituents $R^1$, $R^2$, $R^4$, $R^5$, $R^7$ and $R^8$ are identical or different and are each hydrogen, fluorine, chlorine, bromine, iodine, $C_1$–$C_{20}$-alkyl, —$OR^{10}$, —$SR^{10}$, —$N(R^{10})_2$, —$P(R^{10})_2$ or $Si(R^{10})_3$, where $R^{10}$ are identical or different and are each $C_1$–$C_{10}$-alkyl, $C_6$–$C_{15}$-aryl, $C_3$–$C_{10}$-cycloalkyl, alkylaryl, 3- to 8-membered cycloalkyl which may in turn bear a $C_1$–$C_{10}$-alkyl radical such as methyl, ethyl, propyl as substituent. Examples of such cycloalkyl radicals are cyclopropyl, cyclopentyl, preferably cyclohexyl, norbornyl. The substituents $R^1$, $R^2$, $R^4$, $R^5$, $R^7$ and $R^8$ may also be $C_6$–$C_{15}$-aryl such as phenyl or naphthyl; alkylaryl having from 1 to 10 carbon atoms in the alkyl part and from 6 to 20 carbon atoms in the aryl part, e.g. p-tolyl; arylalkyl having from 1 to 10 carbon atoms in the alkyl part and from 6 to 20 carbon atoms in the, aryl part, e.g. benzyl or neophyl; or triorganosilyl such as $Si(R^{10})_3$, where $R^{10}$ are identical or different and are each $C_1$–$C_{20}$-alkyl, $C_3$–$C_{10}$-cycloalkyl, $C_6$–$C_{15}$-aryl, for example trimethylsilyl, tert-butyldimethylsilyl, triphenylsilyl. The radicals mentioned can of course also be partially or fully substituted by heteroatoms, for example by S—, N—, O— or halogenatom-containing structural elements. Examples of such substituted radicals $R^1$, $R^2$, $R^4$, $R^5$, $R^7$ and $R^8$ are the trifluoromethyl, pentafluoroethyl, heptafluoropropyl, heptafluoroisopropyl and pentafluorophenyl groups.

Preferred substituents $R^1$ and $R^8$ are ones which take up a large amount of space. Such substituents are usually referred to as bulky substituents, and they can cause steric hindrance.

In general, these groups are carboorganic or organosilicon radicals which take up a large amount of space (bulky radicals) or else fluorine and preferably chlorine, bromine and iodine. The number of carbon atoms in such carboorganic or organosilicon radicals is usually not less than three.

Preferred nonaromatic, bulky radicals are carboorganic or organosilicon radicals whch are branched in the α or higher position. Examples of such radicals are branched $C_3$–$C_{20}$-aliphatic radicals, $C_9$–$C_{20}$-araliphatic radicals and $C_3$–$C_{10}$-cycloaliphatic radicals, e.g. isopropyl, tert-butyl, isobutyl, neopentyl, 2-methyl-2-phenylpropyl (neophyl), cyclohexyl, 1-methylcyclohexyl, bicyclo[2.2.1]hept-2-yl (2-norbornyl), bicyclo[2.2.1]hept-1-yl (1-norbornyl), adamantyl. Further suitable radicals of this type are organosilicon radicals having from three to thirty carbon atoms, for example trimethylsilyl, triethylsilyl, triphenylsilyl, tert-butyldimethylsilyl, tritolylsilyl or bis(trimethylsilyl)methyl;

Preferred aromatic, bulky groups are generally $C_6$–$C_{20}$-aryl radicals such as phenyl, 1- or 2-naphthyl or preferably $C_1$–$C_{10}$-alkyl- or $C_3$–$C_{10}$-cycloalkyl-substituted aromatic radicals such as 2,6-dimethylphenyl, 2,6-di-tert-butylphenyl, mesityl.

Very particularly preferred substituents $R^1$ and $R^8$ are i-propyl, tert-butyl, trimethylsilyl, cyclohexyl, i-butyl, trifluoromethyl, 3,5-dimethylphenyl.

In the preferred substitution pattern, $R^1$ and $R^8$ in the formula (I) are identical.

Preferred substituents $R^2$, $R^4$, $R^5$ and $R^7$ are identical or different and are each hydrogen or $C_1$–$C_{20}$-alkyl. The radicals $R^1$ and $R^2$ or $R^7$ and $R^8$ can also be joined to one another so as to form saturated, partially saturated or unsaturated cyclic groups having from 4 to 15 carbon atoms.

Particular preference is given to the radicals $R^2$ and $R^7$ being identical and each being hydrogen and $R^4$ and $R^5$ being as defined above.

The substituents $R^3$ and $R^6$ are, according to the present invention, identical or different and are each hydrogen, alkoxide —$OR^{11}$, thiolate —$SR^{11}$, amine —$N(R^{11})_2$, —$P(R^{11})_2$, or $Si(R^{11})_3$, where $R^{11}$ are identical or different and are each $C_1$–$C_{10}$-alkyl, $C_3$–$C_{10}$-cycloalkyl, in particular 3- to 8-membered cycloalkyl which may in turn bear a $C_1$–$C_{10}$-alkyl radical such as methyl, ethyl or propyl as substituent. Examples of such cycloalkyl radicals are cyclopropyl, cyclopentyl, preferably cyclohexyl, norbornyl. Furthermore, $R^{11}$ may also be a halogen-substituted alkyl or cycloalkyl radical, for example trifluoromethyl, pentafluoroethyl, heptafluoropropyl or heptafluoroisopropyl.

$R^3$ and $R^6$ are preferably alkoxide —$OR^{11}$, thiolate —$SR^{11}$ or amine —$N(R^{11})_2$, where $R^{11}$ is methyl, ethyl, n-propyl, isopropyl, tert-butyl, cyclopropyl, cyclopentyl, cyclohexyl, norbornyl.

Very particular preference is given to $R^{11}$ being methyl. $R^3$ and $R^6$ in the formula (I) are particularly preferably methoxy, ethoxy, isopropyloxy, tert-butyloxy, cyclopropyloxy or cyclohexyloxy.

Possible bridging units Y are the following:

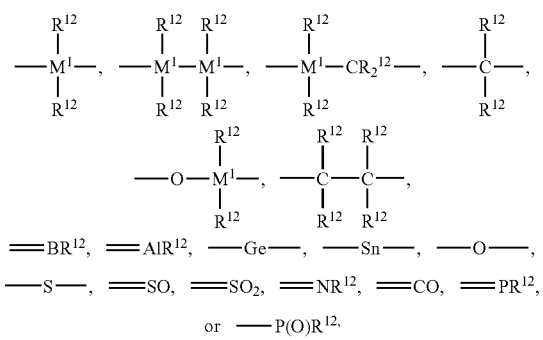

where $R^{12}$ are identical or different and are each a hydrogen atom, a halogen atom, a $C_1$–$C_{10}$-alkyl group, a $C_1$–$C_1$-fluoroalkyl group, a $C_6$–$C_{10}$-fluoroaryl group, a $C_6$–$C_{10}$-aryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group or $R^{12}$ and $R^{13}$ or $R^{12}$ and $R^{14}$ in each case together with the atoms connecting them form a ring, and $M^1$ is silicon, germanium or tin.

Preferred bridging units Y are methylene —$CH_2$—, S, O, —$C(CH_3)_2$—; the bridging units Y are very particularly preferably identical and are oxygen —O—.

The bridged transition metal complexes (I) are generally prepared by methods known to those skilled in the art.

The synthesis of the bridged transition metal phenoxide complexes is described, for example, in C. J. Schaverien, J. Am. Chem. Soc. (1995), pages 3008 to 3012. A well-suited procedure has been found to be the following, which is generally carried out in the temperature range from −78 to 110° C., preferably initially at about 20° C. and the reaction is then completed by boiling under reflux. The biphenol is firstly deprotonated in a solvent, for example tetrahydrofuran (THF), for example by means of sodium hydride or n-butyllithium, and the transition metal compound, for example the halide such as titanium tetrachloride, zirconium tetrachloride or hafnium tetrachloride, advantageously in the form of the bis-THF adduct, is subsequently added. After the reaction is complete, the product is generally obtained by crystallization after salts have been separated off.

The bridged transition metal complexes (I) of the present invention generally still contain from 1 to 4 equivalents of a Lewis base which is generally introduced via the synthetic route. Examples of such Lewis bases are ethers such as diethyl ether or tetrahydrofuran (THF) and also amines such as TMEDA However, the transition metal complexes can also be obtrained free of Lewis bases, for example by drying under reduced pressure or by choice of other solvents in the synthesis. Such measures are known to those skilled in the art.

The novel racemic ansa-metallocene biphenoxide complexes of the formula (II) are prepared by reacting the bridged transition metal complexes (I) with cyclopentadienyl derivatives of the alkali metals or alkaline earth metals and subsequently heating the resulting reaction mixture, in the presence or absence of free radicals or free radical formers, as described below.

Preference is given to using transition metal complexes (I) in which M is zirconium and the radicals $R^3$ and $R^6$ have the above-described, preferred meanings. Very well suited complexes (I) are dichlorozirconium 3,3'-di-tert-butyl-5,5'-dimethoxy-1,1'-bi-2-phenoxide, dichlorozirconium 3,3'-di-tert-butyl-5,5'-diethoxy-1,1'-bi-2-phenoxide, dichlorozirconium 3,3'-di-tert-butyl-5,5'-dipropyloxy-1,1'-bi-2-phenoxide, dichlorozirconium 3,3'-di-tert-butyl-5,5'-dimethylthio-1,1'-bi-2-phenoxide, di-chlorozirconium 3,3'-di-tert-butyl-5,5'-diethylthio-1,1'-bi-2-phenoxide, dichlorozirconium 3,3'-di-tert-butyl-5,5'-dipropylthio-1,1'-bi-2-phenoxide and the zirconium biphenoxide compounds mentioned in the examples.

Possible cyclopentadienyl derivatives of the alkali metals or alkaline earth metals are in principle those which after reaction with the bridged transition metal complexes (I) used according to the present invention selectively give racemic metallocene complexes which are virtually free of meso isomers.

Well suited cyclopentadienyl derivatives of alkali metals or alkaline earth metals are compounds of the formula (III)

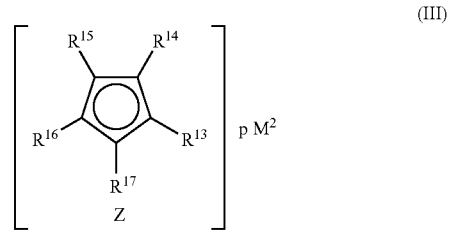

(III)

where the substituents and indices have the following meanings:
$M^2$ is Li, Na, K, Rb, Cs, Be, Mg, Ca, Sr, Ba,
where p=1 in the case of Be, Mg, Ca, Sr, Ba and
p=2 in the case of Li, Na, K, Rb, Cs, and
$R^{13}$ to $R^{17}$ are identical or different and are each hydrogen, $C_1$–$C_{20}$-alkyl, 5- to 7-membered cycloalkyl which may in turn bear a $C_1$–$C_{10}$-alkyl group as substituent, $C_6$–$C_{15}$-aryl or arylalkyl, where adjacent radicals may together form cyclic groups having from 4 to 15 carbon atoms, or $Si(R^{18})_3$, where
$R^{18}$ are identical or different and are each $C_1$–$C_{10}$-alkyl, $C_6$–$C_{15}$-aryl or $C_3$–$C_{10}$-cycloalkyl, and
Z is

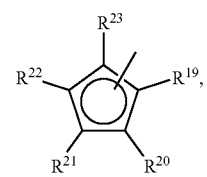

where the radicals
$R^{19}$ to $R^{23}$ are identical or different and are each hydrogen, $C_1$–$C_{20}$-alkyl, 5- to 7-membered cycloalkyl which may in turn bear a $C_1$–$C_{10}$-alkyl group as substituent, $C_6$–$C_{15}$-aryl or arylalkyl, where adjacent radicals may together form cyclic groups having from 4 to 15 carbon atoms, or $Si(R^{24})_3$, where
$R^{24}$ are identical or different and are each $C_1$–$C_{10}$-alkyl, $C_6$–$C_{15}$-aryl or $C_3$–$C_{10}$-cycloalkyl,
or the radicals
$R^{16}$ and Z together form a -[T($R^{25}$)($R^{26}$)]$_m$-E- group, where T can be identical or different and is silicon, germanium, tin or carbon,
$R^{25}$, $R^{26}$ are each hydrogen, $C_1$–$C_{10}$-alkyl, $C_3$–$C_{10}$-cycloalkyl or $C_6$–$C_{15}$-aryl,
m is 1, 2, 3 or 4, and
E is

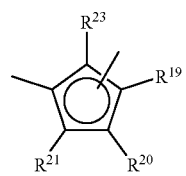

or A, where
A is

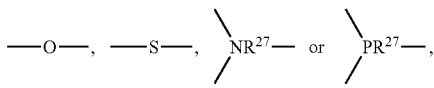

where $R^{27}$ are identical or different and are each $C_1$–$C_{10}$-alkyl, $C_6$–$C_{15}$-aryl, $C_3$–$C_{10}$-cycloalkyl, alkylaryl or $Si(R^{28})_3$,
where $R^{28}$ are identical or different and are each $C_1$–$C_{10}$-alkyl, $C_6$–$C_{15}$-aryl, $C_3$–$C_{10}$-cycloalkyl or alkylaryl.

Preferred compounds of the formula (III) are those in which $M^2$ is lithium, sodium and in particlar magnesium. Further preference is given, to compounds of the formula (III a)

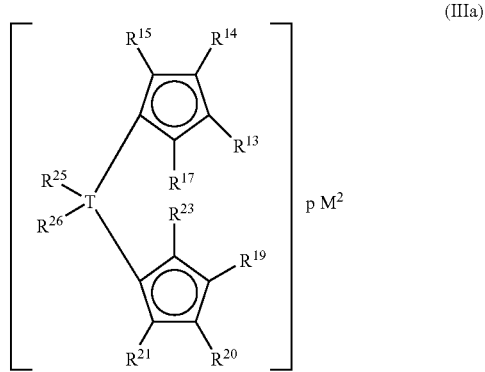

where all substituents are as defined above, and
$M^2$ is an alkali metal ion or alkaline earth metal ion,
where
p is 1 when $M^2$ is an alkaline earth metal ion and is 2 when $M^2$ is an alkali metal ion.

Particular preference is given to compounds of the formula (IIIa), in which $M^2$ is magnesium and $R^{17}$ and $R^{23}$ are hydrogen or different substituents such as $C_1$–$C_{10}$-alkyl, e.g. methyl, ethyl, n-propyl, i-propyl, n-butyl, sec-butyl, tert-butyl, i-butyl, hexyl, also $C_6$–$C_{10}$-aryl such as phenyl or trialkylsilyl such as trimethylsilyl, $T(R^{25}R^{26})$ is bis-$C_1$–$C_{10}$-alkylsilyl or bis-$C_6$–$C_{10}$-arylsilyl, e.g. dimethylsilyl, diphenylsilyl, also 1,2-ethanediyl, methylene, and the radicals $R^{13}$ to $R^{15}$ and $R^{19}$ to $R^{25}$ and p are as defined above and in particular form an indenyl-type ring system or a benzoindenyl-type ring system.

Very particularly preferred compounds III are those which are described in the examples and also
dimethylsilanediylbis(3-tert-butyl-5-methylcyclopentadienyl)magnesium
diethylsilanediylbis(3-tert-butyl-5-methylcyclopentadienyl)magnesium
dimethylsilanediylbis(3-tert-butyl-5-ethylcyclopentadienyl)magnesium
dimethylsilanediylbis(3-tert-pentyl-5-methylcyclopentadienyl)magnesium
dimethylsilanediylbis(2,4,7-trimethylindenyl)magnesium
1,2-ethanediylbis(1-{2,4,7-trimethylindenyl})magnesium
dimethylsilanediylbis(1-indenyl)magnesium
dimethylsilanediylbis(4,5,6,7-tetrahydro-1-indenyl)magnesium
dimethylsilanediylbis(2-methylindenyl)magnesium
phenyl(methyl)silanediylbis(2-methylindenyl)magnesium
diphenylsilanediylbis(2-methylindenyl)magnesium
dimethylsilanediylbis(2-methyl-4,5,6,7-tetrahydro-1-indenyl)magnesium
dimethylsilanediylbis(2,4dimethyl-6-isopropylindenyl)magnesium
dimethylsilanediylbis(2-methyl-1-benzindenyl)magnesium
dimethylsilanediylbis(2-ethyl-1-benzindenyl)magnesium
dimethylsilanediylbis(2-propyl1-benzindenyl)magnesium
dimethylsilanediylbis(2-phenyl-1-benzindenyl)magnesium
diphenylsilanediylbis(2-methyl-1-benzindenyl)magnesium
phenylmethylsilanediylbis(2-methyl-1-benzindenyl)magnesium
ethanediylbis(2-methyl-1-benzindenyl)magnesium
dimethylsilanediylbis(2-methyl-1-tetrahydrobenzindenyl)magnesium
dimethylsilanediylbis(2-methyl-4-isopropyl-1-indenyl)magnesium
dimethylsilanediylbis(2-methyl-4-phenyl-1-indenyl)magnesium
dimethylsilanediylbis(2-methyl-4-naphthyl-1-indenyl)magnesium
dimethylsilanediylbis(2-methyl-4-{3,5-trifluoromethyl}phenyl-1-indenyl)magnesium
dimethylsilanediylbis(2-ethyl-4-isopropyl-1-indenyl)magnesium
dimethylsilanediylbis(2-ethyl-4-phenyl-1-indenyl)magnesium
dimethylsilanediylbis(2-ethyl-4-naphthyl-1-indenyl)magnesium
dimethylsilanediylbis(2-ethyl-4-{3,5-trifluoromethyl}phenyl-1-indenyl)magnesium
ethanediylbis(2-methyl-4-phenyl-1-indenyl)magnesium
ethanediylbis(2-methyl-4-naphthyl-1-indenyl)magnesium
ethanediylbis(2-methyl-4-{3,5-di-(trifluoromethyl)}phenyl-1-indenyl)magnesium
dimethylsilanediylbis(2-methyl-4-(4'-tert-butylphenyl)indenyl)magnesium
dimethylsilanediylbis(2-methyl-4-(4'-tert-butylphenyl)indenyl)(2-isopropyl-4-(4'-tert-butyl-phenyl)indenyl)magnesium
dimethylsilanediylbis(2-cyclohexyl-4-phenylindenyl)magnesium
dimethylsilanediylbis(2-butyl-4-phenylindenyl)magnesium
dimethylsilanediylbis(2-ethyl-4-(4'-tert-butylphenyl)indenyl)magnesium
dimethylsilanediylbis(2-propyl-4-(4'-tert-butylphenyl)indenyl)magnesium
dimethylgermanediylbis(2-methyl-4-(4'-tert-butylphenyl)indenyl)magnesium
diethylsilanediylbis(2-methyl-4-(4'-tert-butylphenyl)indenyl)magnesium
dimethylsilanediylbis(2-butyl-4-(4'-tert-butylphenyl)indenyl)magnesium
dimethylsilanediyl(2-methyl-4-(4'-tert-butylphenyl)indenyl)(4-(4'-tert-butyl-phenyl)indenyl)magnesium
dimethylsilanediylbis(2-butyl-4-(4'-tert-butylphenyl-6-(4'-tert-butylphenyl)indenyl)magnesium
dimethylsilanediylbis(2-isopropyl-4-(4'-tert-butylphenyl)indenyl)magnesium
dimethylsilanediylbis(2-isopropyl-4-(4'-tert-butylphenyl)indenyl)magnesium
dimethylsilanediyl(2-ethyl-4-(4'-tert-butylphenyl)indenyl)
2-isopropyl-4-(4'-tert-butyl-phenyl)indenyl)magnesium
dimethylsilanediyl(2-methyl-4-naphthylindenyl)(2-isopropyl-4-(4'-tert-butyl-phenyl)indenyl)magnesium and
dimethylsilanediylbis(3-tert-butyl-5-methylcyclopentadienyl)dilithium
diethylsilanediylbis(3-tert-butyl-5-methylcyclopentadienyl)dilithium
dimethylsilanediylbis(3-tert-butyl-5-ethylcyclopentadienyl)dilithium
dimethylsilanediylbis(3-tert-pentyl-5-methylcyclopentadienyl)dilithium
dimethylsilanediylbis(2,4,7-trimethylindenyl)dilithium
1,2-ethanediylbis(1-{2,4,7-trimethylindenyl})dilithium
dimethylsilanediylbis(1-indenyl)dilithium
dimethylsilanediylbis(4,5,6,7-tetrahydro-1-indenyl)dilithium
dimethylsilanediylbis(2-methylindenyl)dilithium
phenyl(methyl)silanediylbis(2-methylindenyl)dilithium
diphenylsilanediylbis(2-methylindenyl)dilithium
dimethylsilanediylbis(2-methyl-4,5,6,7-tetrahydro-1-indenyl)dilithium
dimethylsilanediylbis(2,4-dimethyl-6-isopropylindenyl)dilithium
dimethylsilanediylbis(2-methyl-1-benzindenyl)dilithium
dimethylsilanediylbis(2-ethyl-1-benzindenyl)dilithium
dimethylsilanediylbis(2-propyl-1-benzindenyl)dilithium
dimethylsilanediylbis(2-phenyl-1-benzindenyl)dilithium
diphenylsilanediylbis(2-methyl-1-benzindenyl)dilithium.
phenylmethylsilanediylbis(2-methyl-1-benzindenyl)dilithium
ethanediylbis(2-methyl-1-benzindenyl)dilithium
dimethylsilanediylbis(2-methyl-1-tetrahydrobenzindenyl)dilithium
dimethylsilanediylbis(2-methyl-4-isopropyl-1-indenyl)dilithium
dimethylsilanediylbis(2-methyl-4-phenyl-1-indenyl)dilithium
dimethylsilanediylbis(2-methyl-4-naphthyl-1-indenyl)dilithium
dimethylsilanediylbis(2-methyl-4-{3,5-trifluoromethyl}phenyl-1-indenyl)dilithium
dimethylsilanediylbis(2-ethyl-4-isopropyl-1-indenyl)dilithium
dimethylsilanediylbis(2-ethyl-4-phenyl-1-indenyl)dilithium
dimethylsilanediylbis(2-ethyl-4-naphthyl-1-indenyl)dilithium
dimethylsilanediylbis(2-ethyl-4-{3,5-trifluoromethyl}phenyl-1-indenyl)dilithium
ethanediylbis(2-methyl-4-phenyl-1-indenyl)dilithium
ethanediylbis(2-methyl-4-naphthyl-1-indenyl)dilithium
ethanediylbis(2-methyl-4-{3,5-di(trifluoromethyl)}phenyl-1-indenyl)dilithium
dimethylsilanediylbis(2-methyl-4-(4'-tert-butylphenyl)indenyl)dilithium
dimethylsilanediylbis(2-methyl-4-(4'-tert-butylphenyl)indenyl)(2-isopropyl-4-(4'-tert-butyl-phenyl)indenyl)dilithium
dimethylsilanediylbis(2-cyclohexyl-4-phenylindenyl)dilithium
dimethylsilanediylbis(2-butyl-4-phenylindenyl)dilithium
dimethylsilanediylbis(2-ethyl-4-(4'-tert-butylphenyl)indenyl)dilithium
dimethylsilanediylbis(2-propyl-4-(4'-tert-butylphenyl)indenyl)dilithium
dimethylgermanediylbis(2-meth-4-(4'-tert-butylphenyl)indenyl)dilithium
diethylsilanediylbis(2-methyl-4-(4'-tert-butylphenyl)indenyl)dilithium
dimethylsilanediylbis(2-butyl-4-(4'-tert-butylphenyl)indenyl)dilithium
dimethylsilanediyl(2-methyl-4-(4'-tert-butylphenyl)indenyl)-(4-(4'-tert-butylphenyl)indenyl)dilithium
dimethylsilanediylbis(2-butyl-4-(4'-tert-butylphenyl-6-(4'-tert-butylphenyl)indenyl)dilithium
dimethylsilanediylbis(2-isopropyl-4-(4'-tert-butylphenyl)indenyl)dilithium
dimethylsilanediylbis(2-isopropyl-4-(4'-tert-butylphenyl)indenyl)dilithium
dimethylsilanediyl(2-methyl-4-(4'-tert-butylphenyl)indenyl)-2-isopropyl-4-(4'-tert-butyl-phenyl)indenyl)dilithium
dimethylsilanediyl(2-methyl-4-naphthylindenyl)(2-isopropyl-4-(4'-tert-butyl-phenyl)indenyl)dilithium, and also the respective Lewis base adducts of these compounds with, for example, THF, DME, TMEDA Such alkali metal or alkaline earth metal compounds III can be obtained by methods known from the literature, for example by the preferably stoichiometric reaction of an organometallic compound or a hydride of the alkali metal or alkaline earth metal with the appropriate cyclopentadienyl-type hydrocarbon. Suitable organometallic compounds are, for example, n-butyllithium, di-n-butylmagnesium or (n,s)-dibutylmagnesium.

The reaction of the transition metal complexes (I) with the cyclopentadienyl derivatives of alkali metals or alkaline earth metals, preferably those of the formula III or III a), usually takes place in an organic solvent or suspension medium, preferably in a solvent mixture comprising a Lewis-basic solvent, in the temperature range from −78° C. to 250° C., preferably from 0 to 110° C. Well suited solvents are aliphatic hydrocarbons such as pentane, hexane, heptane, aromatic hydrocarbons such as toluene, ortho-, meta- or para-xylene or isopropylbenzene (cumene), ethers such as tetrahydrofuran (THF), diethyl ether, methyl tert-butyl ether or dimethoxyethane (DME), amines such as diisopropylamine, tetramethylethanediamine (TMEDA) or pyridine.

Well suited solvent mixtures are mixtures of toluene and THF, toluene and DME or toluene and TMEDA, with the Lewis base generally being present in an amount of from 0.1 to 50 mol %, preferably from 1 to 20 mol %, based on the solverit mixture. The molar ratio of the transition metal complex (I) to the cyclopentadienyl derivative of an alkali metal or alkaline earth metal (III) is usually in the range from 0.8:1 to 1:1.2, preferably 1:1.

It has been found that subsequent heating of the reaction mixture, to temperatures in the range from −78 to 250° C., preferably from 20 to 150° C. and in particular from 80 to 110° C., and optionally in the presence of free radicals or free radical formers quickly leads to a high yield, in general from 80 to 100%, preferably from 95 to 100%, of racemic biphenoxide complexes (II) in short reaction times.

Free radicals which may be mentioned are oxygen, 2,2'-6,6'-tetramethylpyrimidine N-oxide (TEMPO). Suitable free radical formers are all organic and inorganic compounds which decompose in the abovementioned temperature range and/or on irradiation to form free radicals, e.g. peroxides, diacyl peroxides such as benzoyl peroxide or acetyl peroxide, peroxydicarbonates, peresters, azoalkanes, nitrites, hypochlorites, polyhalomethanes, N-chloramines. Particular preference is given to using TEMPO. Free radical formers are preferably used when the metallocene (I) contains a benzo-fused indenyl system such as dimethylsilylbis(2-methylbenzoindenyl) as cyclopentadienyl-type ligand.

Furthermore, it has been found that the process of the present invention can be carried out as a "single-vessel process" starting from the cyclopentadiene derivatives without isolation of intermediates, and the process proceeds racemoselectively in high total yields under these conditions. Particular preference is therefore given to carrying out the process of the present invention starting from the cyclopentadiene derivatives without isolation of intermediates after the individual process steps.

In a particularly preferred embodiment, the process of the present invention therefore comprises the following successive steps:

a) deprotonation of cyclopentadiene compounds of the formulae (IVa) and (IVb)

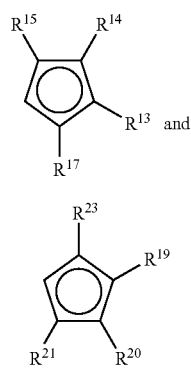

by means of a suitable deprotonating agent, where $R^{13}$, $R^{14}$, $R^{15}$, $R^{17}$ are identical or different and are each hydrogen, $C_1$–$C_{20}$-alkyl, 5- to 7-membered cycloalkyl which may in turn bear a $C_1$–$C_{10}$-alkyl group as substituent, $C_6$–$C_{15}$-aryl or arylalkyl, where adjacent radicals may together form cyclic groups having from 4 to 15 carbon atoms, or $Si(R^{18})_3$, where $R^{18}$ are identical or different and are each $C_1$–$C_{10}$-alkyl, $C_6$–$C_{15}$-aryl or $C_3$–$C_{10}$-cycloalkyl, and $R^{19}$, $R^{20}$, $R^{21}$, $R^{23}$ are identical or different and are each hydrogen, $C_1$–$C_{20}$-alkyl, 5- to 7-membered cycloalkyl which may in turn bear a $C_1$–$C_{10}$-alkyl group as substituent, $C_6$–$C_{15}$-aryl or arylalkyl, where adjacent radicals may together form cyclic groups having from 4 to 15 carbon atoms, or $Si(R^{24})_3$, where $R^{24}$ are identical or different and are each $C_1$–$C_{10}$-alkyl, $C_6$–$C_{15}$-aryl or $C_3$–$C_{10}$-cycloalkyl, b) reaction of the deprotonated compounds (IVa) and (IVb) with a compound $[T(R^{25})(R^{26})]_m Hal_2$, where Hal is a halogen substituent such as F, Cl, Br or I, and subsequent repeat deprotonation by means of a suitable deprotonating agent to form a compound of the formula (IIIa)

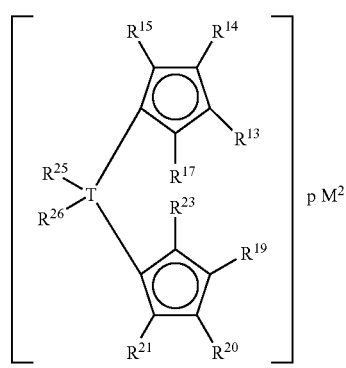

where $M^2$ is an alkali metal ion or alkaline earth metal ion, where p is 1 when $M^2$ is an alkaline earth metal ion and is 2 when $M^2$ is an alkali metal ion, and $R^7$ is as defined above, and T can be identical or different and are each silicon, germanium, tin or carbon, $R^{25}$, $R^{26}$ are each hydrogen, $C_1$–$C_{10}$-alkyl, $C_3$–$C_{10}$-cycloalkyl or $C_6$–$C_{15}$-aryl, and m is 1, 2, 3 or 4;

c) reaction of the compound of the formula (IIIa) with a transition metal complex of the formula (I)

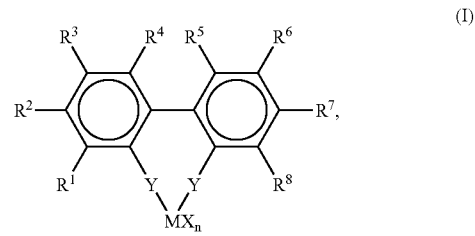

where the substituents and indices are as defined above.

Suitable deprotonating agents include, as indicated above, strong bases and are selected from among n-butyllithium, tert-butyllithium, sodium hydride, potassium tert-butoxide, Grignard reagents of magnesium, magnesium compounds such as, in particular, di-n-butylmagnesium, (n,s)-dibutylmagnesium and other suitable alkaline earth metal alkyl or alkali metal alkyl compounds.

The racemic metallocene complexes of the present invention are preferably compounds of the formula (II)

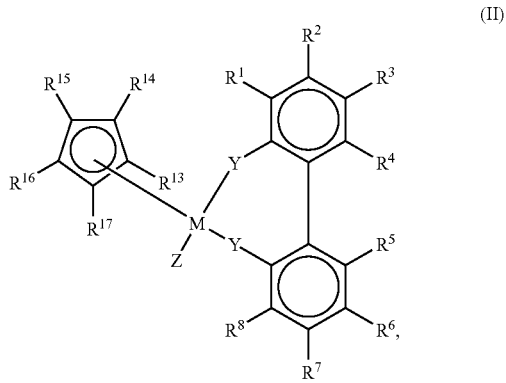

where Y, M and $R^1$ to $R^8$ are as defined above, and $R^{13}$ to $R^{17}$ are identical or different and are each hydrogen, $C_1$–$C_{20}$-alkyl, 5- to 7-membered cycloalkyl which may in turn bear a $C_1$–$C_{10}$-alkyl group as substituent, $C_6$–$C_{15}$-aryl or arylalkyl, where adjacent radicals may together form cyclic groups having from 4 to 15 carbon atoms, or $Si(R^{18})_3$, where $R^{18}$ are identical or different and are each $C_1$–$C_{10}$-alkyl, $C_6$–$C_{15}$-aryl or $C_3$–$C_{10}$-cycloalkyl, and z is

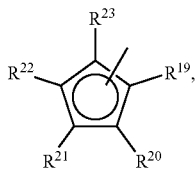

where the radicals
$R^{19}$ to $R^{23}$ are identical or different and are each hydrogen, $C_1$–$C_{20}$-alkyl, 5- to 7-membered cycloalkyl which may in turn bear a $C_1$–$C_{10}$-alkyl group as substituent, $C_6$–$C_{15}$-aryl or arylalkyl, where adjacent radicals may together form cyclic groups having from 4 to 15 carbon atoms, or $Si(R^{24})_3$, where
$R^{24}$ are identical or different and are each $C_1$–$C_{10}$-alkyl, $C_6$–$C_{15}$-aryl or $C_3$–$C_{10}$-cycloalkyl, or the radicals
$R^{16}$ and Z together form a -[T($R^{25}$)($R^{26}$)]$_m$-E- group, where T can be identical or different and are each silicon, germanium, tin or carbon,
$R^{25}$, $R^{26}$ are each hydrogen, $C_1$–$C_{10}$-alkyl, $C_3$–$C_{10}$-cycloalkyl or $C_6$–$C_{15}$-aryl
m is 1, 2, 3 or 4, and
E is

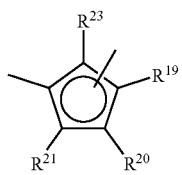

or A, where
A is

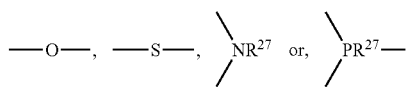

where $R^{27}$ are identical or different and are each $C_1$–$C_{10}$-alkyl, $C_6$–$C_{15}$-aryl, $C_3$–$C_{10}$-cycloalkyl, alkylaryl or $Si(R^{28})_3$
where $R^{28}$ are identical or different and are each $C_1$–$C_{10}$-alkyl, $C_6$–$C_{15}$-aryl, $C_3$–$C_{10}$-cycloalkyl or alkylaryl.

Preferred compounds of the formula (II) are those in which M is titanium, hafnium and in particular zirconium. Preference is also given to bridged compounds of the formula (II), particularly preferably ansa-metallocenes, in which $R^{17}$ and $R^{23}$ are substituents other than hydrogen, e.g. $C_1$–$C_{10}$-alkyl, such as methyl, ethyl, n-propyl, i-propyl, n-butyl, sec-butyl, tert-butyl, i-butyl, hexyl, also $C_6$–$C_{10}$-aryl such as phenyl or trialkylsilyl such as trimethylsilyl, T($R^{25}R^{26}$) is bis-$C_1$–$C_{10}$-alkylsilyl or bis-$C_6$–$C_{10}$-arylsilyl, e.g. dimethylsilyl, diphenylsilyl, also 1,2-ethanediyl, methylene, and the radicals $R^{13}$ to $R^{15}$ and $R^{19}$ to $R^{25}$ are as defined above and in particular form an indenyl-type ring system or a benzoindenyl-type ring system.

Very particularly preferred compounds II are those which are described in the examples and also
dimethylsilanediylbis(3-tert-butyl-5-methylcyclopentadienyl)zirconium 3,3'-di-tert-butyl-5,5'-dimethoxy-1,1'-bi-2-phenoxide;
diethylsilanediylbis(3-tert-butyl-5-methylcyclopentadienyl) zirconium 3,3'-di-tert-butyl-5,5'-dimethoxy-1,1'-bi-2-phenoxide;
dimethylsilanediylbis(3-tert-butyl-5-ethylcyclopentadienyl) zirconium 3,3'-di-tert-butyl-5,5'-dimethoxy-1,1'-bi-2-phenoxide;
dimethylsilanediylbis(3-tert-pentyl-5-methylcyclopentadienyl)zirconium 3,3'-di-tert-butyl-5,5'-dimethoxy-1,1'-bi-2-phenoxide;
dimethylsilanediylbis(2,4,7-trimethylindenyl)zirconium 3,3'-di-tert-butyl-5,5'-dimethoxy-1,1'-bi-2-phenoxide;
1,2-ethanediylbis(1-{2,4,7-trimethylindenyl)}zirconium 3,3'-di-tert-butyl-5,5'-dimethoxy-1,1'-bi-2-phenoxide;
dimethylsilanediylbis(1-indenyl)zirconium 3,3'-di-tert-butyl-5,5'-dimethoxy-1,1'-bi-2-phenoxide;
dimethylsilanediylbis(4,5,6,7-tetrahydro-1-indenyl)zirconium 3,3'-di-tert-butyl-5,5'-dimethoxy-1,1'-bi-2-phenoxide;
dimethylsilanediylbis(2-methylindenyl)zirconium 3,3'-di-tert-butyl-5,5'-dimethoxy-1,1'-bi-2-phenoxide;
phenyl(methyl)silanediylbis(2-methylindenyl)zirconium 3,3'-di-tert-butyl-5,5'-dimethoxy-1,1'-bi-2-phenoxide;
diphenylsilanediylbis(2-methylindenyl)zirconium 3,3'-di-tert-butyl-5,5'-dimethoxy-1,1'-bi-2-phenoxide;
dimethylsilanediylbis(2-methyl-4,5,6,7-tetrahydro-1-indenyl)zirconium 3,3'-di-tert-butyl-5,5'-dimethoxy-1,1'-bi-2-phenoxide;
dimethylsilanediylbis(2,4-dimethyl-6-isopropylindenyl)zirconium 3,3'-di-tert-butyl-5,5'-dimethoxy-1,1'-bi-2-phenoxide;
dimethylsilanediylbis(2-methyl-1-benzindenyl)zirconium 3,3'-di-tert-butyl-5,5'-dimethoxy-1,1'-bi-2-phenoxide
dimethylsilanediylbis(2-ethyl-1-benzindenyl)zirconium 3,3'-di-tert-butyl-5,5'-dimethoxy-1,1'-bi-2-phenoxide;
dimethylsilanediylbis(2-propyl-1-benzindenyl)zirconium 3,3'-di-tert-butyl-5,5'-dimethoxy-1,1'-bi-2-phenoxide;
dimethylsilanediylbis(2-phenyl-1-benzindenyl)zirconium 3,3'-di-tert-butyl-5,5'-dimethoxy-1,1'-bi-2-phenoxide;
diphenylsilanediylbis(2-methyl-1-benzindenyl)zirconium 3,3'-di-tert-butyl-5,5'-dimethoxy-1,1'-bi-2-phenoxide;
phenylmethylsilanediylbis(2-methyl-1-benzindenyl)zirconium 3,3'-di-tert-butyl-5,5'-dimethoxy-1,1'bi-2-phenoxide;
ethanediylbis(2-methyl-1-benzindenyl)zirconium 3,3'-di-tert-butyl-5,5'-dimethoxy-1,1'-bi-2-phenoxide;
dimethylsilanediylbis(2-methyl-1-tetrahydrobenzindenyl) zirconium 3,3'-di-tert-butyl-5,5'-dimethoxy-1,1'-bi-2-phenoxide;
dimethylsilanediylbis(2-methyl-4isopropyl-1-indenyl)zirconium 3,3'-di-tert-butyl-5,5'-dimethoxy-1,1'-bi-2-phenoxide;
dimethylsilanediylbis(2-methyl-4-phenyl-1-indenyl)zirconium 3,3'-di-tert-butyl-5,5'-dimethoxy-1,1'-bi-2-phenoxide;
dimethylsilanediylbis(2-methyl-4-naphthyl-1-indenyl)zirconium 3,3'-di-tert-butyl-5,5'-dimethoxy-1,1'-bi-2-phenoxide;
dimethylsilanediylbis(2-methyl-4-{3,5-trifluoromethyl}phenyl-1-indenyl)zirconium 3,3'-di-tert-butyl-5,5'-dimethoxy-1,1'-bi-2-phenoxide;

dimethylsilanediylbis(2-ethyl-4-isopropyl-1-indenyl)zirconium 3,3'-di-tert-butyl-5,5'-dimethoxy-1,1'-bi-2-phenoxide;
dimethylsilanediylbis(2-ethyl-4-phenyl-1-indenyl)zirconium 3,3'-di-tert-butyl-5,5'-dimethoxy-1,1'-bi-2-phenoxide;
dimethylsilanediylbis(2-ethyl-4-naphthyl-1-indenyl)zirconium 3,3'-di-tert-butyl-5,5'-dimethoxy-1,1'-bi-2-phenoxide;
dimethylsilanediylbis(2-ethyl-4-{3,5-trifluoromethyl}phenyl-1-indenyl)zirconium 3,3'-di-tert-butyl-5,5'-dimethoxy-1,1'-bi-2-phenoxide;
ethanediylbis(2-methyl-4-phenyl-1-indenyl)zirconium 3,3'-di-tert-butyl-5,5'-dimethoxy-1,1'-bi-2-phenoxide;
ethanediylbis(2-methyl-4-naphthyl-1-indenyl)zirconium 3,3'-di-tert-butyl-5,5'-dimethoxy-1,1'-bi-2-phenoxide;
ethanediylbis(2-methyl-4-{3,5-di(trifluoromethyl)}phenyl-1-indenyl)zirconium 3,3'-di-tert-butyl-5,5'-dimethoxy-1,1'-bi-2-phenoxide;
dimethylsilanediylbis(2-methyl-4-(4'-tert-butylphenyl)indenyl)zirconium 3,3'-di-tert-butyl-5,5'-dimethoxy-1,1'-bi-2-phenoxide;
dimethylsilanediyl(2-methyl-4-(4'-tert-butylphenyl)indenyl)(2-isopropyl-4-(4'-tert-butyl-phenyl)indenyl)zirconium 3,3'-di-tert-butyl-5,5'-dimethoxy-1,1'-bi-2-phenoxide;
dimethylsilanediylbis(2-cyclohexyl-4-phenylindenyl)zirconium 3,3'-di-tert-butyl-5,5'-dimethoxy-1,1'-bi-2-phenoxide;
dimethylsilanediylbis(2-butyl-4-phenylindenyl)zirconium 3,3'-di-tert-butyl-5,5'-dimethoxy-1,1'-bi-2-phenoxide;
dimethylsilanediylbis(2-ethyl-4-(4'-tert-butylphenyl)indenyl)zirconium 3,3'-di-tert-butyl-5,5'-dimethoxy-1,1'-bi-2-phenoxide;
dimethylsilanediylbis(2-propyl-4-(4'-tert-butylphenyl)indenyl)zirconium 3,3'-di-tert-butyl-5,5'-dimethoxy-1,1'-bi-2-phenoxide;
dimethylgermanediylbis(2-methyl-4-(4'-tert-butylphenyl)indenyl)zirconium 3,3'-di-tert-butyl-5,5'-dimethoxy-1,1'-bi-2-phenoxide;
diethylsilanediylbis(2-methyl-4-(4'-tert-butylphenyl)indenyl)zirconium 3,3'-di-tert-butyl-5,5'-dimethoxy-1,1'-bi-2-phenoxide;
dimethylsilanediylbis(2-butyl-4-(4'-tert-butylphenyl)indenyl)zirconium 3,3'-di-tert-butyl-5,5'-dimethoxy-1,1'-bi-2-phenoxide;
dimethylsilanediyl(2-methyl-4-(4'-tert-butylphenyl)indenyl)-4-(4'-tert-butyl-phenyl)indenyl)zirconium 3,3'-di-tert-butyl-5,5'-dimethoxy-1,1'-bi-2-phenoxide;
dimethylsilanediylbis(2-butyl-4-(4'-tert-butylphenyl)-6-(4'-tert-butylphenyl)indenyl)zirconium 3,3'-di-tert-butyl-5,5'-dimethoxy-1,1'-bi-2-phenoxide;
dimethylsilanediylbis(2-isopropyl-4-(4'-tert-butylphenyl)indenyl)zirconium 3,3-di-tert-butyl-5,5'-dimethoxy-1,1'-bi-2-phenoxide;
dimethylsilanediyl(2-ethyl-4-(4'-tert-butylphenyl)indenyl)(2-isopropyl-4-(4'-tert-butyl-phenyl)indenyl)zirconium 3,3'-di-tert-butyl-5,5'-dimethoxy-1,1'-bi-2-phenoxide; and
dimethylsilanediyl(2-methyl-4-naphthylindenyl)(2-isopropyl-4-(4'-tert-butyl-phenyl)indenyl)zirconium 3,3'-di-tert-butyl-5,5'-dimethoxy-1,1'-bi-2-phenoxide.

The racemic metallocene complexes, preferably those of the formula (II), can generally be modified further.

For example, the biphenoxide ligand in the complex II can, in particular, be replaced in a substitution reaction and, if desired, be reused. Suitable substitution methods are reaction of the racemic metallocene complexes, preferably those of the formula (II), with $SOCl_2$, silicon tetrachloride, methylaluminum dichloride, dimethylaluminum chloride, aluminum trichloride, dialkylaluminum chlorides, aluminum sesquichlorides, particularly preferably ethylaluminum dichloride, or a Brönsted acid such as a hydrogen halide, i.e. HF, HBr, Hl, preferably HCl, which is generally employed as such or as a solution in water or organic solvents such as diethyl ether, THF. Well suited solvents are aliphatic hydrocarbons such as pentane, hexane, heptane, aromatic hydrocarbons such as toluene, ortho-, meta- or para-xylene or isopropylbenzene (cumene), ethers such as tetrahydrofuran (THF), diethyl ether, methyl tert-butyl ether or dimethoxyethane (DME), amines such as diisopropylamine, tetramethylethanediamine (TMEDA) or pyridine.

Very useful solvents are Lewis base-containing solvent mixtures of hydrocarbons and ethers or amines or both, for example mixtures of toluene and THF, toluene and DME or toluene and TMEDA, with the Lewis base generally being present in an amount of 0.01–50 mol %, preferably 0.1–10 mol %, based on the solvent mixture. Particularly well suited "replacement reagents" are carboxylic acid halides such as acetyl chloride, phenylacetyl chloride, 2-thiophenacetyl chloride, trichloroacetyl chloride, trimethylacetyl chloride, O-acetylmandelyl chloride, 1,3,5-benzenetricarboxylic chloride, 2,6-pyridinecarboxylic chloride, tert-butylacetyl chloride, chloroacetyl chloride, 4-chlorophenylacetyl chloride, dichloroacetyl chloride, 3-methoxyphenylacetyl chloride, acetyl bromide, bromoacetyl bromide, acetyl fluoride, benzoyl fluoride, with these generally being used in the abovementioned solvents or else as such.

This substitution reaction usually gives the dihalide analogous to the compound of the formula (II).

A further well suited substitution method is the reaction of the racemic metallocene complexes of the formula (II) with organoaluminum compounds such as tri-$C_1$–$C_{10}$-alkylaluminums, i.e. trimethylaluminum, triethylaluminum, tri-n-butylaluminum, triisobutylaluminum. According to the present state of knowledge, this generally gives the organo compound analogous to II (organic radicals in place of the biphenoxide, e.g. $C_1$–$C_{10}$-alkyl, such as methyl, ethyl, n-butyl, i-butyl) and, for example, the organoaluminum binaphthoxide.

In the substitution reactions, the components are usually used in the stoichiometric ratio, depending on whether a monosubstituted or disubstituted product is to be obtained.

The substitution reactions generally take place with retention of the stereochemistry of the metallocene complexes, i.e. it is generally the case that no conversion of the racemic form into the meso form of the metallocene complexes takes place. Rather, particularly in the case of the above-described chlorination methods, the rac selectivity can be increased while generally retaining the stereochemistry of the starting biphenoxide complexes.

The process of the present invention makes it possible for the rac form of metallocene biphenoxide complexes and also the ansa-metallocenes obtainable therefrom to be obtained very selectively. Bridged indenyl- or benzoindenyl-type metallocenes which have a ligand other than hydrogen in the vicinity of the bridging unit (namely the 2 position) can be obtained particularly advantageously from the biphenoxide complexes of the present invention.

The racemic metallocene complexes of the present invention, in particular those of the formula II or their above-described derivatives obtainable by, for example, replacement of the biphenoxide ligand, can be used as catalysts or in catalyst systems for the -polymerization of olefinically unsaturated compounds such as ethylene, propylene, 1-butene, 1-hexene, 1-octene, styrene. They are particularly advantageous for the stereoselective polymerization of prochiral, olefinically unsaturated compounds such as propylene, styrene. Suitable catalysts or catalyst systems in whch the racemic metallocene complexes of the present invention can function as "metallocene component" are usually obtained by means of compounds capable of forming metallocenium ions, as described, for example, in EP-A-0 700 935, page 7, line 34 to page 8, line 21, and the formulae (IV) and (V) therein. Further compounds capable of forming metallocenium ions are aluminoxanes $(RAlO)_n$ such as methylaluminoxane.

The racemic metallocene complexes of the present invention, in particular those of the formula (II) or their above-described derivatives obtainable by, for example, replacement of the biphenoxide ligand, can also be used as reagents or as catalysts or in catalyst systems in stereoselective, in particular organic, synthesis. Examples which may be mentioned are stereoselective reductions or stereoselective alkylations of C=C double bonds or C=O, C=N double bonds.

EXAMPLES

Abbreviations
bp=1,1'-bi-2-phenoxide
bip=3,3',5,5'-tetra-t-butyl-1,1'-bi-2-phenoxide
bap=3,3'-di-tert-butyl-5,5'-dimethoxy-1,1'-bi-2-phenoxide General procedures: Preparation and handling of the organometallic compounds were carried out in the absence of air and moisture under argon (Schlenk technique or glove box). All solvents required were purged with argon and dried over molecular sieves before use.

$bpH_2$, is commercially available from Acros Organics (151995000), 3,5-di-t-butylphenol from Aldrich (D4,850-8) and 3-t-butyl-5-methoxyphenol from Acros Organics (235235000). $bipH_2$ and $bapH_2$ were prepared as described in EP 35965. The silyl-bridged indenes were synthesized as described in U.S. Pat. No. 4,985,576.

Example 1: (Comparative Example)

Preparation of dimethylsilylbis(2-methyl-indenyl) zirconium 3,3',5,5'-tetra-tert-butyl-1,1'-bi-2-phenoxide a) Preparation of $ZrCl_4(THF)_2$ In a dry 500 ml three-neck round-bottom flask which had been flushed with inert gas and was provided with a dropping funnel and vacuum connection with stopcock, 8.52 g (36.56 mmol) of $ZrCl_4$ were suspended in 125 ml of toluene. The suspension was cooled to about 4° C. in an ice bath, and 7 g of THF were subsequently added slowly via the dropping funnel over a period of 15 minutes. The resulting suspension was allowed to warm to room temperature and was stirred for one hour.

b) Preparation of $bipLi_2$

In a dry 500 ml three-neck round-bottom flask which had been flushed with inert gas and was provided with a dropping funnel and vacuum connection with stopcock, 15.9 g (36.53 mmol) of $bipH_2$ were dissolved in 150 ml of toluene and 7.0 g of THF. The solution was cooled to about 4° C. in an ice bath and 27.5 ml of a BuLi solution were subsequently added via the dropping funnel over a period of 15 minutes. The reaction mixture was then allowed to warm to room temperature and was stirred for one hour.

c) Preparation of $(THF)_2Cl_2Zr(bip)$

The solution from step b) was transferred under nitrogen by means of a syringe into the suspension from step a) at room temperature over a period several minutes. The residual $bipLi_2$ was rinsed in using 10 ml of toluene. The reaction mixture was stirred at room temperature for 5 hours. The mixture was subsequently heated to 80° C.

d) Preparation of $Me_2Si(2-Me-ind)Li_2$

In a dry 1000 ml three-neck round-bottom flask which had been flushed with inert gas and was provided with a dropping funnel and vacuum connection with stopcock, 11.2 g (35.53 mmol) of dimethylsilylbis(2-methylindenyl) were suspended in 130 ml of toluene and 7.0 g of THF. At room temperature, 26.5 ml of a BuLi solution were slowly added dropwise over a period of 20 minutes while stirring. The resulting suspension was stirred at room temperature for a further 2 hours and subsequently heated to 80° C.

e) Preparation of $Me_2Si(2-Me-ind)_2Zr(bip)$

The suspension from step c) was transferred at 80° C. under nitrogen by means of a syringe into the suspension from step d) at 80° C. over a period of several minutes. Residues of the zirconium compound from step c) were rinsed in using 10 ml of toluene. The resulting suspension was heated to 100° C. and stirred at this temperature for 2 hours. The reaction mixture was subsequently cooled to room temperature and stirred for another 60 hours. An $^1$H-NMR spectrum of the reaction mixture showed a rac/meso ratio of about 3:1. The reaction mixture was subsequently heated at 100° C. for a further 3 hours, after which the rac/meso ratio determined by means of $^1$H-NMR was about 5:1. The mixture was subsequently stirred at 100° C. for a further 5 hours. The $^1$H-NMR spectrum of the reaction mixture then showed a rac/meso ratio of about 19:1. The suspension was transferred while hot by means of a syringe to a glass filter frit No. 4 and filtered into a 1000 ml round-bottom flask with stopcock. The precipitate was washed twice with 25 ml of toluene and the filtrate was subsequently concentrated at 40° C. under reduced pressure. 360 ml of solvent were removed. The complex crystallized out at room temperature. After cooling at −20° C. for six days, the precipitate was filtered off, washed with 20 ml of toluene and dried under reduced pressure. This gave a total of 17.32 g of the target compound in pure rac form, as was established by means $^1$H-NMR. Yield: 50.4%.

Example 2

Preparation of dimethylsilylbis(2-methylindenyl) zirconium 3,3'-di-tert-butyl-5,5'-dimethoxy-1,1'bi-2-phenoxide a) Preparation of $ZrCl_4(THF)_2$ The preparation was carried out as described in step a) of Example 1, but the amounts used were 8.85 g of $ZrCl_4$ (37.97 mmol), 115 ml of toluene and 7 g of THF.

b) Preparation of $bapLi_2$

In a dry 500 ml three-neck round-bottom flask which had been flushed with inert gas and was provided with a dropping funnel and vacuum connection with stopcock, 13.61 g of $bapH_2$ were dissolved in 115 ml of toluene and 7.0g of THF. 29 ml of a 20% strength by weight BuLi solution were slowly added dropwise to the solution via the dropping funnel. After addition was complete, the mixture was stirred for one hour.

c) Preparation of (THF)$_2$Cl$_2$Zr(bap)

The suspension from step a) was transferred under nitrogen by means of a syringe into the suspension from step c) at room temperature over a period of several minutes. Residues of bapLi$_2$ were washed out using 10 ml of toluene and added. The reaction mixture was stirred at room temperature for three hours and subsequently heated to 80° C.

d) Preparation of Me$_2$Si(2-Me-ind)Li$_2$

This reaction step was carried out as in Example 1, d). The amounts used were 11.5 g (36.33 mmol) of dimethylsilylbis (2-methylindenyl), 115 ml of toluene and 7.0 g of THF. 28.0 ml of a 20% strength by weight BuLi solution were added. The mixture was subsequently heated to 80° C.

e) Preparation of Me$_2$Si(2-Me-ind)$_2$Zr(bap)

The suspension from step c) was transferred at 80° C. under nitrogen by means of a syringe into the suspension from step d) at 80° C. over a period of several minutes. Residues of the zirconium compound were rinsed in using 10 ml of toluene. The resulting suspension was heated to 100° C. and stirred at this temperature for three hours. $^1$H-NMR spectroscopy indicated complete isomerization of the complex into the rac form. The reaction mixture was filtered through a glass filter frit No. 4 into a 1000 ml round-bottom flask with stopcock and the filtrate was concentrated at 40° C. under reduced pressure. 370 ml of solvent were removed. The target complex crystallized out at room temperature and was isolated by decantation and dried under reduced pressure. This gave a total of 17.59 g of the target complex in the pure rac form. Yield: 63.5%.

Comparison of Examples 1 and 2 shows that for an identical bisindenyl ligand, the metallocene biphenoxide complex can be obtained in a significantly shorter reaction time when using the process of the present invention. Furthermore, the metallocene biphenoxide complex of the present invention can be isolated in higher yield in a simple manner at room temperature in Example 2. The introduction of the polar methoxy substituents on the biphenoxide substituent alters the electronic structure of the ligand so that the solubility of the resulting novel metallocene biphenoxide complex in toluene is significantly reduced compared to the tetra-tert-butyl-substituted biphenoxide complex, which makes isolation considerably easier.

Example 3

Preparation of dimethylsilylbis(2-methylbenzindenyl)zirconium 3,3',5,5'tetra-tert-butyl-1,1'-bi-2-phenoxide a) Preparation of ZrCl$_4$(DME)

In a dry 500 ml three-neck round-bottom flask which had been flushed with inert gas and was provided with a dropping funnel and vacuum connection with stopcock, 6.3 g (27.03 mmol) of ZrCl$_4$ were suspended in 110 ml of toluene. The suspension was cooled to 4° C. in an ice bath and 6.0 g of DME were slowly added dropwise via the dropping funnel over a period of 15 minutes. The resulting suspension was allowed to warm to room temperature and was stirred for one hour.

b) Preparation of bipLi$_2$

In a dry 500 ml three-neck round-bottom flask which had been flushed with inert gas and was provided with a dropping funnel and vacuum connection with stopcock, 11.10 g (27.03 mmol) of bipH$_2$ were dissolved in 200 ml of toluene and 6.0 g of DME. The solution was cooled to about 4° C. in an ice bath. 25 ml of a 20% strength by weight BuLi solution were subsequently added via the dropping funnel over a period of 15 minutes. The mixture was subsequently allowed to warm to room temperature and was stirred for a further one hour. The reaction mixture was heated to 50° C., stirred at this temperature for 2 hours and cooled back to room temperature.

c) Preparation of (THF)$_2$Cl$_2$Zr(bip)

The suspension from b) was transferred under nitrogen by means of a syringe into the white suspension from step a) at room temperature over a period of several minutes. The residues of bipLi$_2$ were washed out using 10 ml of toluene and added. The reaction mixture was stirred at room temperature for 12 hours. Since $^1$H-NMR spectroscopy indicated that the reaction was not yet complete, the suspension was heated to 80° C., which virtually completed the reaction.

d) Preparation of Me$_2$Si(2-Me-benzind)Li$_2$

In a dry 1000 ml three-neck round-bottom flask which had been flushed with inert gas and was provided with a dropping funnel and vacuum connection with stopcock, 10.70 g (25.68 mmol) of dimethylsilylbis(2-methylbenzindenyl) were suspended in 120 ml of toluene and 6.0 g of DME. At room temperature, 19.5 ml of a 20% strength by weight BuLi solution were slowly added dropwise over a period of 20 minutes. The suspension was heated to 80° C. and stirred for a further 2 hours.

e) Preparation of Me$_2$Si(2-Me-benzind)Zr(bip)

The suspension from step c) was transferred at 80° C. under nitrogen by means of a syringe into the suspension from step d) at 80° C. over a period of several minutes. Residues of the zirconium compound were washed out using 10 ml of toluene and added. The resulting suspension was heated to 100° C. and stirred at this temperature for 3 hours. It was subsequently cooled to room temperature. A $^1$H-NMR spectrum showed that the target complex had been formed in a rac/meso ratio of about 1.9:1. The suspension was stirred at room temperature for another 12 hours, then heated at 100° C. for 8 hours. A further $^1$H-NMR spectrum showed that the complex had isomerized to a rac/meso ratio of about 3.9:1.

Example 4

Preparation of dimethylsilylbis(2-methylbenzindenyl)zirconium 3,3'-di-tert-butyl-5,5'-dimethoxy-1, 1'bi-2-phenoxide a) Preparation of ZrCl$_4$(DME)

The synthesis of the zirconium-DME adduct was carried out as in a) of Example 3. The amounts used were: 12.60 g of zirconium tetrachloride, 150 ml of toluene, 10.0 g of DME.

b) Preparation of bapLi$_2$

In a dry 500 ml three-neck round-bottom flask which had been flushed with inert gas and was provided with a dropping funnel and vacuum connection with stopcock, 19.38 g of bapH$_2$ were dissolved in 200 ml of toluene and 10.0 g of DME. The solution was cooled to about 4° C. in an ice bath and 25 ml of a 20% strength by weight BuLi solution were subsequently added dropwise via the dropping funnel over a period of 15 minutes. After about one third of the BuLi solution had been added, the reaction mixture formed lumps. The reaction mixture was heated to 70° C., resulting in dissolution of the lumps. The remainder of the BuLi solution was added at 70° C. After the addition was complete, a stirrable suspension had been obtained and this was cooled to room temperature.

c) Preparation of (DME)Cl$_2$Zr(bap)

The suspension from step a) was transferred under nitrogen by means of a syringe into the suspension from step b) at room temperature over a period of several minutes. Residues of the zirconium compound were rinsed in using 10 ml of toluene. The reaction mixture was stirred at room temperature for 60 hours. An $^1$H-NMR spectrum showed that the reaction was not complete, so the suspension was heated at 80° C. for 4 hours, after which the reaction was virtually complete.

d) Preparation of Me$_2$Si(2-Me-benzind)Li$_2$

The preparation was carried out as in step d) of Example 3. The amounts used were: 21.4 g of dimethylsilyl-2-methylbenzindenyl, 10.0 g of DME and 39.0 ml of a 20% strength BuLi solution.

e) Preparation of Me$_2$Si(2-Me-benzind)Zr(bip)

The suspension from step c) was transferred at 80° C. under nitrogen by means of a syringe into the suspension from step d) at 80° C. over a period of several minutes. Residues of the zirconium compound were washed out using 10 ml of toluene and added. The resulting suspension was heated to 100° C. and stirred at this temperature for a total of 12 hours. A $^1$H-NMR spectrum showed that the target compound had been formed in a rac/meso ratio of about 9:1.

A comparison of Examples 3 and 4 shows that the use of the methoxy-substituted biphenoxide auxiliary ligand employed according to the present invention leads, under comparable reaction conditions; to a significantly higher rac/meso ratio than does the analogous tert-butyl-substituted compound.

Example 5

Preparation of dimethylsilyl(2-methyl4-(4'-tert-butylphenyl)indenyl)(2-isopropyl4-(4'-tert-butylphenyl)indenyl)zirconium 3,3',5,5'tetra-tert-butyl-1,1'-bi-2-phenoxide a) Preparation of ZrCl4(THF)$_2$ The synthesis of this compound was carried out as described in Example 1. The amounts used were 7.75 g (33.25 mmol) of ZrCl$_4$, 130 ml of toluene, 6.5 g of THF.

b) Preparation of bipLi$_2$

The preparation of this compound was carried out as described in Example 1. The amounts used were: 13.65 g (33.24 mmol) of bipH$_2$, 130 ml of toluene and 6.5 g of THF.

c) Preparation of (THF)$_2$Cl$_2$Zr(bip)

The preparation of this compound was carried out as described in Example 1 c) using the above solutions b) and a). The resulting suspension was heated to 80° C.

d) Preparation of Me$_2$Si(2-Me-4-(4'-t-Bu-Ph)-ind)(2-i-Pr-4-(4'-t-Bu-Ph)-ind)Li$_2$ In a dry 1000 ml three-neck round-bottom flask which had been flushed with inert gas and was provided with a dropping funnel and vacuum connection with stopcock, 19.50 ml of the dimethylsilylbisindenyl ligand were suspended in 150 ml of toluene and 8 g of THF. At room temperature, 24 ml of a 20% strength by weight BuLi solution were slowly added dropwise over a period of 20 minutes. The resulting suspension was heated to 80° C. and stirred for another 1.5 hours.

e) Preparation of the Target Compound

The suspension from c) was transferred at 80° C. under nitrogen by means of a syringe into the suspension from step d) at 80° C. over a period of several minutes. Residues of the zirconium compound were washed out using 10 ml of toluene and added. The resulting solution was stirred at 100° C. for 3 hours. The suspension was subsequently transferred while hot by means of a syringe to a glass filter frit No. 4 and filtered into a 1000 ml round-bottom flask with stopcock. The white precipitate was washed with 10 ml of toluene. The filtrate was evaporated to dryness under reduced pressure, giving 38.9 g (110%) of the crude compound.

Example 6

Preparation of dimethylsilyl(2-methyl-4-(4'-tert-butylphenyl)indenyl)(2-isopropyl-4-(4'-tert-butylphenyl)indenyl)zirconium 3,3'-di-tert-butyl-5,5'-dimethoxy-1,1'bi-2-phenoxide a) Preparation of ZrCl$_4$(THF)$_2$ The preparation of this compound was carried out as described in Example 1. The amounts used were 5.15 g (22.10 mmol) of ZrCl$_4$, 100 ml of toluene and 4.1 g of THF.

b) Preparation of bapLi$_2$

The preparation of this compound was carried out as described in Example 2. The amounts used were 7.92 g (22.10 mmol) of bapH$_2$, 100 ml of toluene, 10 g of THF and 16.5 ml of 20% strength by weight BuLi solution.

c) Preparation of (THF)$_2$Cl$_2$Zr(bap)

The preparation of this compound was carried out as described in Example 2. The resulting suspension was heated to 85° C.

d) Preparation of Me$_2$Si(2-Me-ind)(2-i-Pr-ind)Li$_2$

In a dry 1000 ml three-neck round-bottom flask which had been flushed with inert gas and was provided with a dropping funnel and vacuum connection with stopcock, 13.0 g (21.34 mmol) of the dimethylsilylbisindenyl ligand were suspended in 120 ml of toluene and 6.0 g of THF. At room temperature, 16.0 ml of a 20% strength by weight BuLi solution were slowly added dropwise over a period of 20 minutes. The mixture was subsequently heated to 80° C. and stirred for another 1.5 hours. The suspension was finally heated to 85° C.

e) Preparation of the Target Compound

The suspension from step c) was transferred at 85° C. by means of a syringe into the suspension from step d) at 85° C. over a period of several minutes. Residues of the zirconium compound were washed out using 10 ml of toluene and added. The resulting suspension was heated to 100° C. and stirred at this temperature for 3 hours. A $^1$H-NMR spectrum showed virtually complete formation of the racemate form of the target compound. The suspension was transferred while hot by means of a syringe to a glass filter frit No. 4 and and filtered into a 1000 ml round-bottom flask with stopcock. The precipitate was washed with 10 ml of toluene. The filtrate was concentrated under reduced pressure, with 150 ml of the solvent being removed. The flask was stored at −20° C. for 25 days, resulting in formation of a precipitate. The precipitate was isolated by filtration and drying under reduced pressure, giving a total of 14.37 g (58%) of the pure rac form of the target compound.

Example 7

Preparation of dimethylsilyl(2-methyl-4-(4'-tert-butylphenyl)indenyl)(2-isopropyl-4-(4'-tert-butylphenyl)indenyl)zirconium 1,1'bi-2-phenoxide a) Preparation of $ZrCl_4(THF)_2$ The preparation of this compound was carried out as described in Example 1. The amounts used were 7.61 g (32.65 mmol) of $ZrCl_4$, 120 ml of toluene, 6.5 g of THF.

b) Preparation of $bpLi_2$

In a dry 500 ml three-neck round-bottom flask which had been flushed with inert gas and was provided with a dropping funnel and vacuum connection with stopcock, 6.08 g of 1,1'-bi-2-phenol ($bpH_2$) were dissolved in 110 ml of toluene and 6.5 g of THF. The solution was cooled to about 4° C. in an ice bath, after which 24.5 ml of a 20% strength by weight BuLi solution were slowly added via the dropping funnel over a period of 15 minutes. The suspension was allowed to warm to room temperature and was stirred for another one hour.

c) Preparation of $(THF)_2Cl_2Zr(bp)$

The suspension from b) was transferred under nitrogen by means of a syringe into the suspension from a) at room temperature over a period of several minutes. Residues of $bpLi_2$ were washed out using 10 ml of toluene and added. The suspension was stirred at room temperature for 4 hours and subsequently heated to 85° C.

d) Preparation of $Me_2Si(2-Me-4-(4'-t-Bu-Ph)-ind)(2-i-Pr-4-(4'-t-Bu-Ph)-ind)Li_2$ In a dry 1000 ml three-neck round-bottom flask which had been flushed with inert gas and was provided with a dropping funnel and vacuum connection with stopcock, 19.0 g of the dimethylsilylbisindenyl compound were suspended in 150 ml of toluene and 8.0 g of THF. At room temperature, 23.5 ml of a BuLi solution were slowly added dropwise over a period of 20 minutes. The suspension was subsequently heated to 60° C. and stirred for one hour. The suspension was then heated to 85° C.

e) Preparation of the Target Compound

The suspension from step c) was transferred at 85° C. under nitrogen by means of a syringe into the suspension from step d) at 85° C. over a period of several minutes. Residues of the zirconium compound were washed out using 10 ml of toluene and added. The resulting suspension was stirred at 100° C. for a total of 12 hours and subsequently cooled to about 70° C. A $^1$H-NMR spectrum showed virtually racemoselective formation of the target complex. The reaction mixture was transferred while hot by means of a syringe to a glass filter frit No. 4 and filtered into a 1000 ml round-bottom flask with stopcock. The filtrate was concentrated under reduced pressure, with 350 ml of the solvent being removed. The flask was stored at room temperature for one day, resulting in formation of a precipitate. The precipitate was isolated by filtration and drying under reduced pressure, giving 10.95 g of the pure rac form of the target compound with one equivalent of toluene. Yield: 36%.

The invention claimed is:

1. A process for preparing racemic metallocene complexes by reacting transition metal complexes of the formula (I)

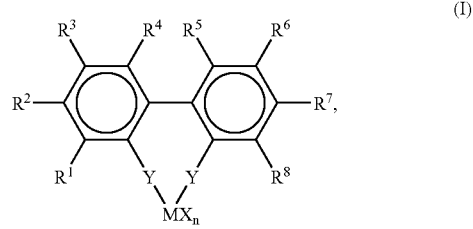

where the substituents and indices have the following meanings:

M is titanium, zirconium, hafnium, vanadium, niobium, tantalum, chromium, molybdenum, tungsten or an element of transition group III of the Periodic Table and the lanthanides, X are identical or different and are each fluorine, chlorine, bromine, iodine, hydrogen, $C_1$–$C_{10}$-alkyl, $C_6$–$C_{15}$-aryl, alkylaryl having from 1 to 10 carbon atoms in the alkyl part and from 6 to 20 carbon atoms in the aryl part, —$OR^9$ or —$NR^9_2$, where $R^9$ are identical or different and are each $C_1$–$C_{10}$-alkyl, $C_6$–$C_{15}$-aryl, $C_3$–$C_{10}$-cycloalkyl, alkylaryl, n is an integer from 1 to 4 and corresponds to the valence of M minus 2, $R^1$, $R^2$, $R^4$, $R^5$, $R^7$, $R^8$ are identical or different and are each hydrogen, fluorine, chlorine, bromine, iodine, $C_1$–$C_{20}$-alkyl, 3- to 8-membered cycloalkyl which may in turn bear a $C_1$–$C_{10}$-alkyl group as substituent, $C_6$–$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part, —$OR^{10}$, —$SR^{10}$, —$N(R^{10})_2$, —$P(R^{10})_2$ or $Si(R^{10})_3$, where $R^{10}$ are identical or different and are each $C_1$–$C_{10}$-alkyl, $C_6$–$C_{15}$-aryl, $C_3$–$C_{10}$-cycloalkyl, alkylaryl, where the radicals mentioned may be partially or fully substituted by heteroatoms, $R^3$, $R^6$ are identical or different and are each hydrogen, —$OR^{11}$, —$SR^{11}$, —$N(R^{11})_2$, —$P(R^{11})_2$ or $Si(R^{11})_3$, where $R^{11}$ are identical or different and are each $C_1$–$C_{10}$-alkyl, $C_3$–$C_{10}$-cycloalkyl, Y are identical or different and are each

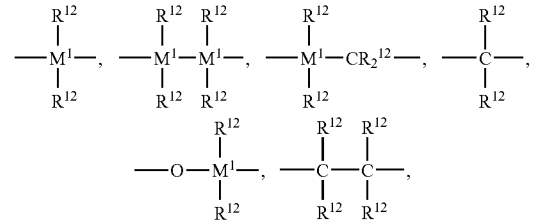

where $R^{12}$ are identical or different and are each hydrogen, halogen, $C_1$–$C_{10}$-alkyl, $C_1$–$C_{10}$-fluoroalkyl, $C_6$–$C_{10}$-fluoroaryl, $C_6$–$C_{10}$-aryl, $C_1$–$C_{10}$-alkoxy, $C_2$–$C_{10}$-alkenyl, $C_7$–$C_{40}$-arylalkyl, $C_8$–$C_{40}$-arylalkenyl, $C_7$–$C_{40}$- alkylaryl, or two radicals R$^{12}$ together with the atoms connecting them form a ring, M$^1$ is silicon, germanium or tin, with cyclopentadienyl derivatives of alkali metals or alkaline earth metals and heating the reaction mixture obtained in this way to a temperature in the range from −78 to 250° C.

2. A process as claimed in claim 1 comprising the following successive steps:

a) deprotonation of compounds of the formulae (IVa) and (IVb)

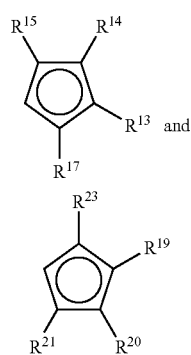

by means of a suitable deprotonating agent, where

R$^{13}$, R$^{14}$, R$^{15}$, R$^{17}$ are identical or different and are each hydrogen, C$_1$–C$_{20}$-alkyl, 5- to 7-membered cycloalkyl which may in turn bear a C$_1$–C$_{10}$-alkyl group as substituent, C$_6$–C$_{15}$-aryl or arylalkyl, where adjacent radicals may together form cyclic groups having from 4 to 15 carbon atoms, or Si(R$^{18}$)$_3$, where R$^{18}$ are identical or different and are each C$_1$–C$_{10}$-alkyl, C$_6$–C$_{15}$-aryl or C$_3$–C$_{10}$-cycloalkyl, and R$^{19}$, R$^{20}$, R$^{21}$, R$^{23}$ are identical or different and are each hydrogen, C$_1$–C$_{20}$-alkyl, 5- to 7-membered cycloalkyl which may in turn bear a C$_1$–C$_{10}$-alkyl group as substituent, C$_6$–C$_{15}$-aryl or arylalkyl, where adjacent radicals may together form cyclic groups having from 4 to 15 carbon atoms, or Si(R$^{24}$)$_3$, where R$^{24}$ are identical or different and are each C$_1$–C$_{10}$-alkyl, C$_6$–C$_{15}$-aryl or C$_3$–C$_{10}$-cycloalkyl, b) reaction of the deprotonated compounds (IVa) and (IVb) with a compound [T(R$^{25}$)(R$^{26}$)]$_m$Hal$_2$, where Hal is a halogen substituent such as F, Cl, Br or I, and subsequent repeat deprotonation by means of a suitable deprotonating agent to form a compound of the formula (IIIa)

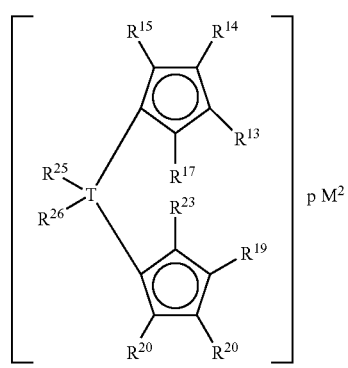

where

M$^2$ is an alkali metal ion or alkaline earth metal ion, where p is 1 when M$^2$ is an alkaline earth metal ion and is 2 when M$^2$ is an alkali metal ion, and T can be identical or different and are each silicon, germanium, tin or carbon, R$^{25}$, R$^{26}$ are identical or different and are each hydrogen, C$_1$–C$_{10}$-alkyl, C$_3$–C$_{10}$-cycloalkyl or C$_6$–C$_{15}$-aryl, and m is 1, 2, 3 or 4;

c) reaction of the compound of the formula (IIIa) with a transition metal complex of the formula (I)

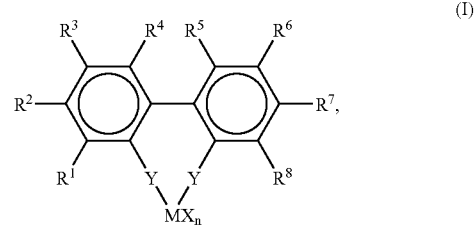

where the substituents and indices are as defined in claim 1.

3. A process as claimed in claim 2, wherein the deprotonating agent is n-butyllithium, tert-butyllithium, sodium hydride, potassium tert-butoxide, Grignard reagents of magnesium, magnesium compounds, suitable alkaline earth metal alkyl compounds or alkali metal alkyl compounds.

4. A process as claimed in claim 2 which is carried out without isolation of intermediates after individual process steps.

5. A process as claimed in claim 2, wherein, in the compounds of the formula (IIIa), M$^2$ is magnesium and R$^{17}$ and R$^{23}$ are each hydrogen, C$_1$–C$_{10}$-alkyl, C$_6$–C$_{10}$-aryl, trialkylsilyl, and T(R$^{25}$R$^{26}$) is bis-C$_1$–C$_{10}$-alkylsilyl, or bis-C$_6$–C$_{10}$-arylsilyl, 1,2-ethanediyl or methylene; and the radicals R$^{13}$ to R$^{15}$ and R$^{19}$ to R$^{21}$ form, an indenyl-type ring system or a benzindenyl-type ring system.

6. A process as claimed in claim 1, wherein the reaction of the cyclopentadienyl derivatives with compounds of the formula (I) is carried out with addition of free radicals or free radical formers to the reaction mixture.

7. A process as claimed in claim 1, wherein R$^1$ and R$^8$ in the formula (I) are bulky substituents.

8. A process as claimed in claim 1, wherein R$^3$ and R$^6$ in the formula (I) are each methoxy, ethoxy, isopropyloxy, tert-butyloxy, cyclopropyloxy or cyclohexyloxy.

9. A process as claimed in claim 1, wherein the bridging units Y in the formula (I) are identical and are each oxygen.

10. A process as claimed in claim 1, wherein cyclopentadienyl derivatives of magnesium or lithium are used.

11. A racemic metallocene complex of the formula (II)

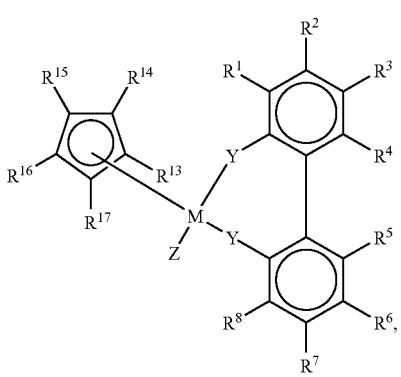

where Y, M and $R^1$ to $R^8$ are as defined in claim 1, and $R^{13}$ to $R^{17}$ are identical or different and are each hydrogen, $C_1$–$C_{20}$-alkyl, 5-to 7-membered cycloalkyl which may in turn bear a $C_1$–$C_{10}$-alkyl group as substituent, $C_6$–$C_{15}$-aryl or arylalkyl, where adjacent radicals may together form cyclic groups having from 4 to 15 carbon atoms, or $Si(R^{18})_3$, where
$R^{18}$ are identical or different and are each $C_1$–$C_{10}$-alkyl, $C_6$–$C_{15}$-aryl or $C_3$–$C_{10}$-cycloalkyl, and
Z is

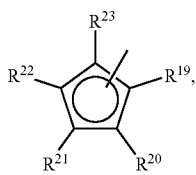

where the radicals
$R^{19}$ to $R^{23}$ are identical or different and are each hydrogen, $C_1$–$C_{20}$-alkyl, 5- to 7-membered cycloalkyl which may in turn bear a $C_1$–$C_{10}$-alkyl group as substituent, $C_6$–$C_{15}$-aryl or arylalkyl, where adjacent radicals may together form cyclic groups having from 4 to 15 carbon atoms, or $Si(R^{24})_3$ where
$R^{24}$ are identical or different and are each $C_1$–$C_{10}$-alkyl, $C_6$–$C_{15}$-aryl or $C_3$–$C_{10}$-cycloalkyl,
or the radicals
$R^{16}$ and Z together form a -[T($R^{25}$)($R^{26}$)]$_m$-E- group, where
T may be identical or different and are each silicon, germanium, tin or carbon,
$R^{25}$, $R^{26}$ are each hydrogen, $C_1$–$C_{10}$-alkyl, $C_3$–$C_{10}$-cycloalkyl or $C_6$–$C_{15}$-aryl
m is 1, 2, 3 or 4, and
E is

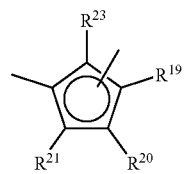

or A, where
A is

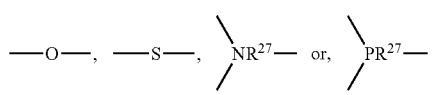

where $R^{27}$ are identical or different and are each $C_1$–$C_{10}$-alkyl, $C_6$–$C_{15}$-aryl, $C_3$–$C_{10}$-cycloalkyl, alkylaryl or $Si(R^{28})_3$
where $R^{28}$ are identical or different and are each $C_1$–$C_{10}$-alkyl, $C_6$–$C_{15}$-aryl, $C_3$–$C_{10}$-cycloalkyl or alkylaryl.

12. A racemic metallocene complex as claimed in claim 11 in which $R^{17}$ and $R^{23}$ are not hydrogen when $R^{16}$ and Z together form a -[T($R^{25}$)($R^{26}$)]$_m$-E-group.

13. A catalyst which comprises the racemic metallocene as claimed in claim 11.

14. A catalyst which comprises the racemic metallocene as claimed in claim 12.

15. A process as claimed in claim 5 wherein $R^{17}$ and $R^{23}$ are methyl, ethyl, n-propyl, i-propyl, n-butyl, sec-butyl, tert-butyl, i-butyl, hexyl, phenyl, or trimethylsilyl and T($R^{25}R^{26}$) is dimethylsilyl, diphenylsilyl, 1,2-ethanediyl or methylene.

16. A process as claimed in claim 15 wherein the reaction of the cyclopentadienyl derivatives with compounds of the formula (I) is carried out with addition of free radicals or free radical formers to the reaction mixture, and wherein $R^1$ and $R^8$ in the formula (I) are bulky substituents, $R^3$ and $R^6$ in the formula (I) are each methoxy, ethoxy, isopropyloxy, tert-butyloxy, cyclopropyloxy or cyclohexyloxy, the bridging units Y in the formula (I) are identical and are each oxygen, and cyclopentadienyl derivatives of magnesium or lithium are used.

17. The process as claimed in claim 3, wherein the magnesium compounds are di-n-butylmagnesium, (n,s)-dibutylmagnesium, and mixtures thereof.

18. The process as claimed in claim 5, wherein the $C_6$–$C_{10}$-aryl is phenyl.

19. The process as claimed in claim 5, wherein the trialkylsilyl is trimethylsilyl.

* * * * *

UNITED STATES PATENT AND TRADEMARK OFFICE
CERTIFICATE OF CORRECTION

PATENT NO. : 7,193,099 B2  
APPLICATION NO. : 10/532570  
DATED : March 20, 2007  
INVENTOR(S) : Hans-Robert-Hellmuth Damrau et al.

It is certified that error appears in the above-identified patent and that said Letters Patent is hereby corrected as shown below:

At col. 28, line 62 claim 1, after the Drawing and before "where" insert
--= $BR^{12}$, = $AlR^{12}$, –Ge–, –Sn–, –O–, –S–, = SO, = $SO_2$, = $NR^{12}$, = CO, = $PR^{12}$ or = $P(O)R^{12}$--

At col. 29, lines 51-66 claim 2, delete Drawing (IIIa) and insert instead:

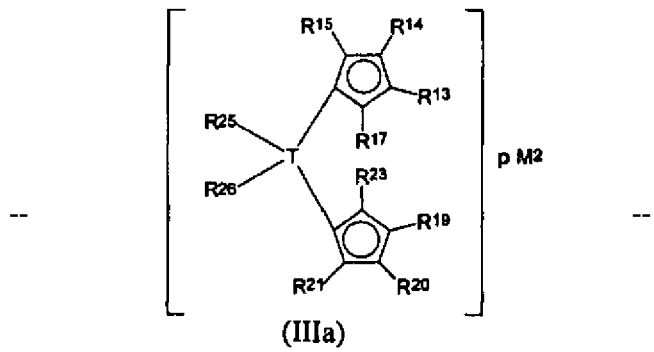

(IIIa)

At Col. 30, line 37 claim 3, delete "suitable"

Signed and Sealed this

First Day of September, 2009

David J. Kappos  
*Director of the United States Patent and Trademark Office*